(12) United States Patent
Eberwein et al.

(10) Patent No.: US 12,648,867 B2
(45) Date of Patent: *Jun. 9, 2026

(54) GARMENT FOR STABILIZING A HUMAN ANATOMICAL JOINT

(71) Applicant: Stoko Design Inc., Vancouver (CA)

(72) Inventors: Zachary Eberwein, North Vancouver (CA); Kevin Reilly, Vancouver (CA); Scott Morgan, North Vancouver (CA); Nick Rutckyj, Vancouver (CA)

(73) Assignee: Stoko Design Inc., Vancouver (CA)

( * ) Notice: Subject to any disclaimer, the term of this patent is extended or adjusted under 35 U.S.C. 154(b) by 1123 days.

This patent is subject to a terminal disclaimer.

(21) Appl. No.: 16/677,268

(22) Filed: Nov. 7, 2019

(65) Prior Publication Data

US 2020/0146866 A1 May 14, 2020

Related U.S. Application Data

(60) Provisional application No. 62/758,549, filed on Nov. 10, 2018.

(51) Int. Cl.
 *A61F 5/01* (2006.01)
(52) U.S. Cl.
 CPC .................................. *A61F 5/0123* (2013.01)
(58) Field of Classification Search
 CPC ............ A41D 13/1254; A41D 13/0543; A41D 31/185; A61F 2005/0181;
 (Continued)

(56) References Cited

U.S. PATENT DOCUMENTS

| | | | | |
|---|---|---|---|---|
| 4,089,064 A | * | 5/1978 | Chandler, Jr. ......... | A41B 11/14 2/404 |
| 4,116,236 A | | 9/1978 | Albert | |

(Continued)

FOREIGN PATENT DOCUMENTS

| | | | |
|---|---|---|---|
| JP | 2002-514105 A | 5/2002 | |
| JP | 2008163523 A | 7/2008 | |

(Continued)

OTHER PUBLICATIONS

European Patent Office European Search Report (EP 19 88 1722), corresponding to the subject matter of the present application. Date of Mailing; Jul. 13, 2022.

(Continued)

*Primary Examiner* — Ophelia A Hawthorne
(74) *Attorney, Agent, or Firm* — Kevin R. Erdman; Brannon Sowers & Cracraft PC

(57) ABSTRACT

The present invention involves a garment for enveloping at least in part a joint, for example a knee of a leg. Comprising a belt disposed to fit about a body part, for example the waist, of the user, a plurality of inextensible web portions and a tension member are disposed longitudinally along a corresponding predetermined curved three-dimensional spatial path within or on a matrix of a garment fabric along the leg. The path spatially relates the first tension member to at least one natural ligament of the knee, at least one of the plurality of inextensible web portions being disposed to apply pressure to the medial side of the knee. The tension member is anchored by the triceps surae of the leg and to the belt via a tensioner. A second tension member may be incorporated in the garment leg to apply pressure to the lateral side of the knee.

20 Claims, 22 Drawing Sheets

(58) Field of Classification Search
CPC ...... A61F 2005/0179; A61F 2005/0167; A61F
2005/0155; A61F 5/0109; A63B 71/1225
See application file for complete search history.

(56) References Cited

U.S. PATENT DOCUMENTS

| | | | |
|---|---|---|---|
| 4,216,547 A * | 8/1980 | Picchione ............ | A41D 31/185 |
| | | | 2/22 |
| 4,862,523 A | 9/1989 | Lipov | |
| 5,308,305 A * | 5/1994 | Romney ............ | A63B 21/4021 |
| | | | 482/121 |
| 8,533,864 B1 * | 9/2013 | Kostrzewski ...... | A41D 13/0015 |
| | | | 2/69 |
| 2006/0130215 A1 | 6/2006 | Torry | |
| 2010/0095422 A1 | 4/2010 | Lopez et al. | |
| 2015/0032040 A1 | 1/2015 | Cadichon | |
| 2015/0074865 A1 | 3/2015 | Yamada et al. | |
| 2015/0305909 A1 | 10/2015 | Kausek | |
| 2018/0338547 A1 | 11/2018 | Celestrin Carmona | |

FOREIGN PATENT DOCUMENTS

| | | |
|---|---|---|
| JP | 2014-508010 A | 4/2014 |
| WO | 1998036713 A1 | 8/1998 |
| WO | 2012125765 A2 | 9/2012 |
| WO | 2018083468 A1 | 5/2018 |

OTHER PUBLICATIONS

Canadian Intellectual Property Office, International Search Report (PCT/CA2019/051584), corresponding to the subject matter of the present application. Date of Mailing; Feb. 5, 2020.
Canadian Intellectual Property Office, International Written Opinion (PCT/CA2019/051584), corresponding to the subject matter of the present application. Date of Mailing; Feb. 5, 2020.
Canadian Patent Office, International Search Report, mailed Mar. 6, 2019 (PCT/CA2018/051591).
Canadian Patent Office, International Search Written Opinion, mailed Mar. 6, 2019 (PCT/CA2018/051591).
Japanese Patent Office, Preliminary Rejection of Japanese Patent Application No. 2020-533048 (corresponding to the priority U.S. Appl. No. 16/216,668 of the present application), dated Oct. 27, 2022.
National Intellectual Property Administration of China (CNIPA) First Office Action (CN 201980069179.7), corresponding to the subject matter of the present application. Date of Mailing; Mar. 6, 2023.
Japan Patent Office: Japanese Office Action (JP 2021-523477), corresponding to the subject matter of the present application. Date of Mailing; Jun. 3, 2024.

* cited by examiner

1210

1227b

1229b

1221b

1240a

1212

1221a

1223b

1231b

1225a

1225b

1233b

1220b

1220a

1200

1310

1312

1321b

1325b

1320b

1300

1340a

1321a

1327a

1329a

1323a

1333a

1331a

1325a

1320a 1728b
1628b
1640b
1740b
1628a
1822a
1728a
1628a
1728a
1724a
1730a
1726a
1626a
1800

1810
1812
1728b
1728b
1628b
1624b
1630b
1626b
1726b
1728a
1628b
1630b
1730a
1726a
1626b 1624a    1660    1660

1660    1660

1660

1660

1628a

1630a'

1670

1628a

1670

1660    1660

1628a

1624a

1630a''    1660

1630a'''

GARMENT FOR STABILIZING A HUMAN ANATOMICAL JOINT

CROSS-REFERENCE TO RELATED APPLICATIONS

This present invention claims priority under 35 USC 119(e) to U.S. Provisional Patent Application Ser. No. 62/758,549, filed Nov. 10, 2018, and is related to the inventions disclosed in U.S. Provisional Patent Application Ser. Nos. 62/599,675 and 62/640,513; filed Dec. 15, 2017, and Mar. 8, 2018, respectively; U.S. non-Provisional patent application Ser. No. 16/216,668, filed Dec. 11, 2018; and PCT International Patent Application Serial No. PCT/CA2018/051591, filed Dec. 13, 2018; the disclosures of which are incorporated by reference herein.

BACKGROUND OF THE INVENTION

Field of the Invention

This present invention relates to the medical field as exemplified by IPC class A61 and more particularly to apparatus and associated methods for stabilizing articulating joints of the human body, including devices adapted to facilitate walking. In one aspect, it relates to an apparatus for stabilizing the human knee and the operation of such an apparatus configured and arranged for treating damaged ligaments in the knee.

Description of the Related Art

Orthopedic braces are used to stabilize joints between the limbs of the human anatomy in cases where the joints or the limbs articulating about them have sustained damage. Braces have been employed to stabilize knees, ankles, elbows and wrists in this way. The brace is applied to reduce strain on the injured limb or joint while permitting the limb or joint to still perform its function, thereby minimizing the risk of further damage.

Several knee brace products have been developed to more specifically protect the ligaments of the knee, including the anterior cruciate ligament (ACL), posterior cruciate ligament (PCL), and medial collateral ligament (MCL). These are the ligaments most often damaged in when knees are overstrained, particularly by individuals involved in strenuous sporting activity. The lateral collateral ligament (LCL) may also sometimes become strained. The brace products for protecting these ligaments vary greatly in technology, function, and efficacy.

Some products are focused on providing mechanical encapsulation that still allows articulation of the joint. Such products tend to involve rather heavy hinge mechanisms and are generally bulky and not particularly aesthetic. At the other extreme there are several products that assume the form of a garment, different forms of such garments employing different technologies to produce compressive forces in the general vicinity of the knee in an attempt to stabilize it and protect the above ligaments. Some garments fall short in providing enough compression. Others provide adequate overall compression but do not direct the compression to key anatomical areas.

There thus remains a need for a garment capable of accurately directing adequate force to stabilize an injured articulating human anatomical joint.

SUMMARY OF THE INVENTION

In a first embodiment of a garment for stabilizing a human knee, the garment is arranged for enveloping at least in part a first knee of a first leg of a human user, the garment comprising a belt disposed to fit about the waist of the user, a plurality of inextensible web portions and a first tension member disposed longitudinally along a corresponding predetermined first curved three-dimensional spatial path within or on a matrix of a garment fabric along the first leg, the first predetermined path spatially relating the first tension member to at least one natural ligament of the first knee, at least one of the plurality of inextensible web portions being disposed by the first tension member to apply pressure to one of the medial and the lateral side of the first knee. The first tension member may have a proximal end and a lateral end, the proximal end of the first tension member anchored to the belt and the distal end of the first tension member disposed to be anchored by a triceps surae of the first leg of the user.

The distal end of the first tension member may disposed to be anchored by the triceps surae of the user via a loop of the tension member extending more than once around the first leg of the user, the loop disposed to encircle the first leg of the user below the triceps surae of the first leg of the user. In other embodiments, the distal end of the first tension member may be disposed to be anchored by the triceps surae of the first leg of the user via a loop of the tension member disposed to extend about the triceps surae of the first leg of the user on one of the medial and lateral side of the first leg of the user and the at least one of the plurality of inextensible web portions may be disposed to apply pressure to the other of the medial and the lateral side of the first knee of the user. The proximal end of the first tension member may be anchored to the belt via a tensioner. The tensioner is may be an adjustable tensioner disposed and configured to allow the tension in the first tension member to be adjusted.

The first tension member may comprise a plurality of the inextensible web portions and tensionable fasteners. In other embodiments, the first tension member may comprise an inextensible cable extending along and within one or more hollow guides within or on the matrix of the garment fabric and on or within the matrix of the plurality of inextensible web portions. The cable may cross over itself on or in the at least one of the plurality of inextensible web portions disposed to apply pressure to one of the medial and the lateral side of the knee.

The garment may further comprise a tension regulator for maintaining a tension in the first tension member when the first knee of the first leg of the human user is bent. The tension regulator may comprise a pulley affixed to an inextensible web portion disposed between the first knee and the waist of the user proximate the first knee.

The garment may further comprise a second tension member disposed longitudinally along a corresponding second predetermined curved three-dimensional spatial path within or on a matrix of a garment fabric along the first leg of the user, the second predetermined path spatially relating the second tension member to at least one natural ligament of the second knee, at least one of the plurality of inextensible web portions being disposed by the second tension member to apply pressure to the other of the medial and the lateral side of the second knee. The second tension member may have a proximal end and a lateral end, the proximal end of the second tension member anchored to the belt and the distal end of the second tension member disposed to be anchored by a triceps surae of the first leg of the user. In other embodiments, the distal ends of both the first and the second tension members may terminate in a joint inextensible web portion surrounding the first leg below the triceps surae of the first leg.

The garment may be further arranged for enveloping at least in part a second knee of a corresponding second leg of the user, the garment comprising a third tension member disposed longitudinally along a corresponding third predetermined curved three-dimensional spatial path within or on a matrix of a garment fabric along the second leg of the user, the third predetermined path spatially relating the third tension member to at least one natural ligament of the second knee, at least one of the plurality of inextensible web portions being disposed by the third tension member to apply pressure to one of the medial and the lateral side of the second knee.

In a more general sense, the embodiments of the brace garment are arranged for enveloping at least in part a first joint of a first appendage of a human user, the garment comprising a belt disposed to fit about a body part of the user, a plurality of inextensible web portions, and a first tension member disposed longitudinally along a corresponding predetermined first curved three-dimensional spatial path within or on a matrix of a garment fabric along the first appendage, the first predetermined path spatially relating the first tension member to at least one natural ligament of the first joint, at least one of the plurality of inextensible web portions being disposed by the first tension member to apply pressure to one of a first and a second side of the first joint.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1:
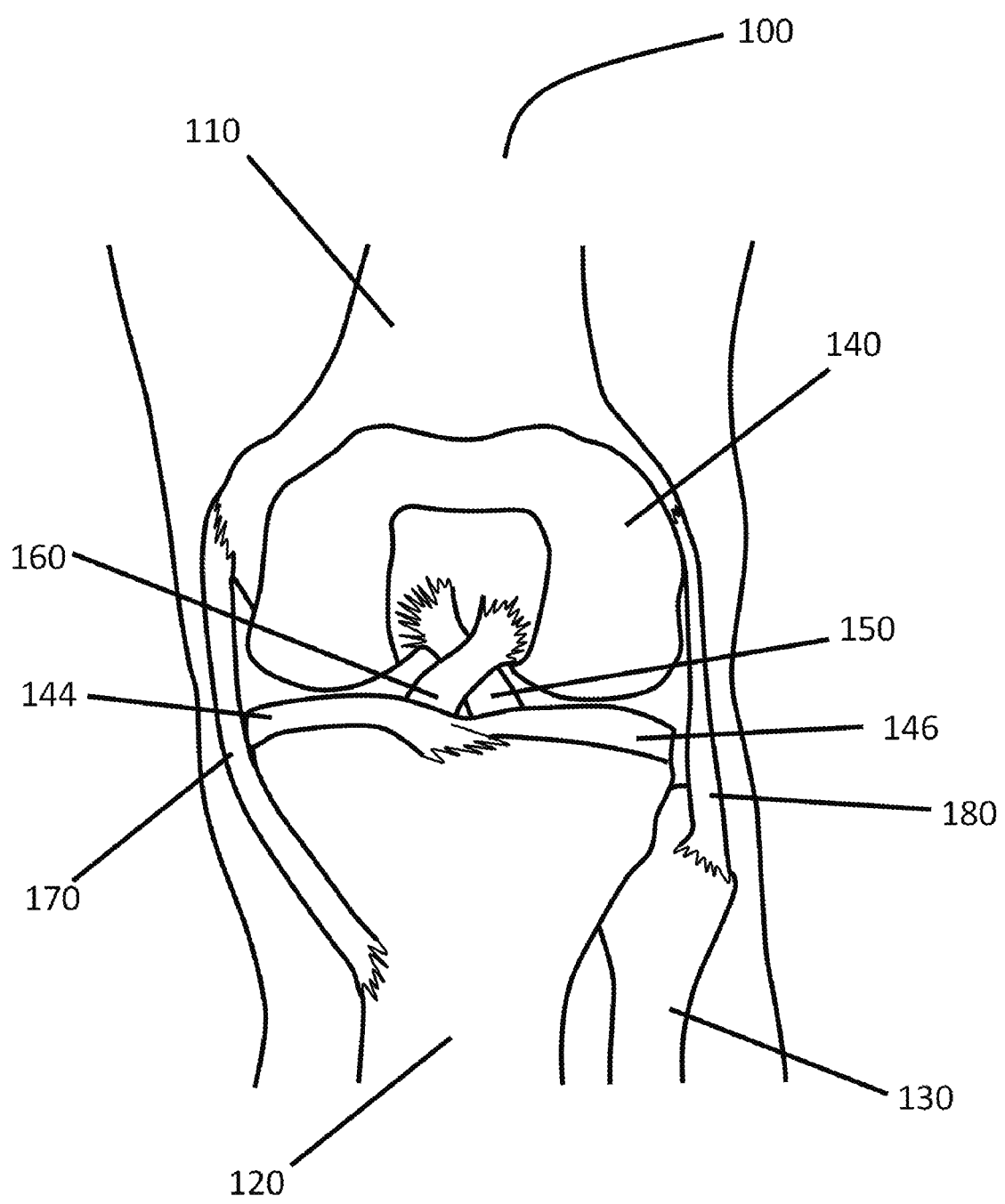
FIG. 1 is a drawing showing the general structure of the human left knee with the patella and its adhesions deleted for the sake of clarity.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize their teachings.

The present invention relates to a garment incorporating a brace arrangement for an articulating joint of a human body. In some embodiments, the brace comprises tensionable segments of inextensible material disposed to exert force on at least one natural ligament of the joint. In other embodiments, tension members disposed within conduits in segments of inextensible material provide the required force. In order to describe the garment and brace, we consider first the human knee as shown in FIG. 1.

FIG. 1 shows internal knee portion 100 of the human left leg as viewed from the front or anterior, but with the patella or knee cap and its various adhesions removed for the sake of clarity of the internal structure of this particular joint. The major bones of the leg are shown as femur 110, tibia 120 and fibula 130. The portions of these bones that have to contact one another during articulation are provided with articular cartilage 140, the two portions of the cartilage on tibia 120 being medial meniscus 144 and lateral meniscus 146. The bones are stabilized with respect to one another by strategically placed ligaments that hold them together. These include posterior cruciate ligament (PCL) 150 and anterior cruciate ligament (ACL) 160 binding together interacting faces of femur 110 and tibia 120, and medial collateral ligament (MCL) 170 and lateral collateral ligament (LCL) 180 binding respectively tibia 120 and fibula 130 to respectively the medial and lateral portions of the head of femur 110. The human right knee is substantially a mirror image of the left knee with respect to the medial plane.

Figure 2A:
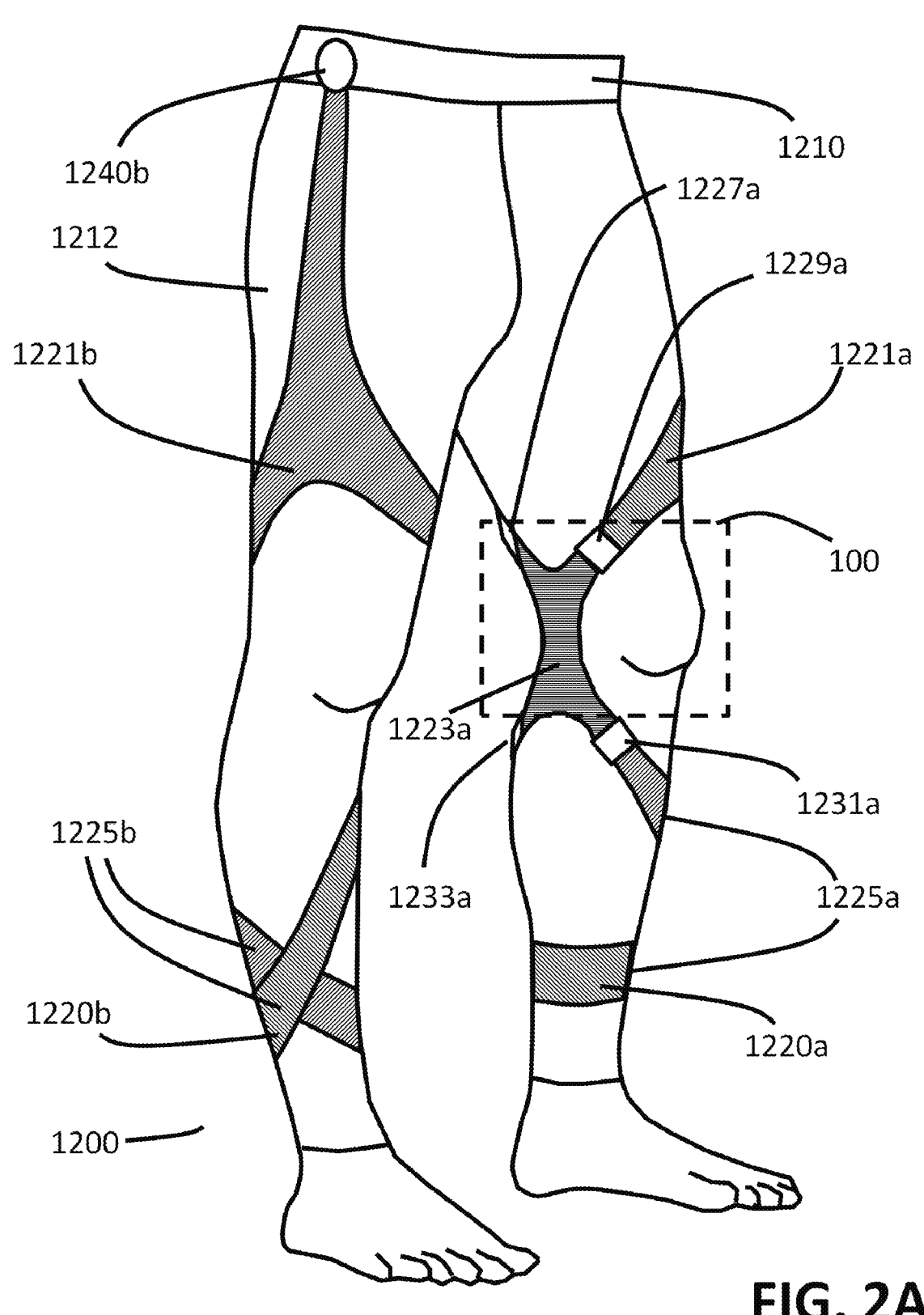
FIG. 2A and FIG. 2B are drawings showing different views of a first embodiment of a medial collateral ligament bracing garment for protecting the human knee.
Figure 2B:
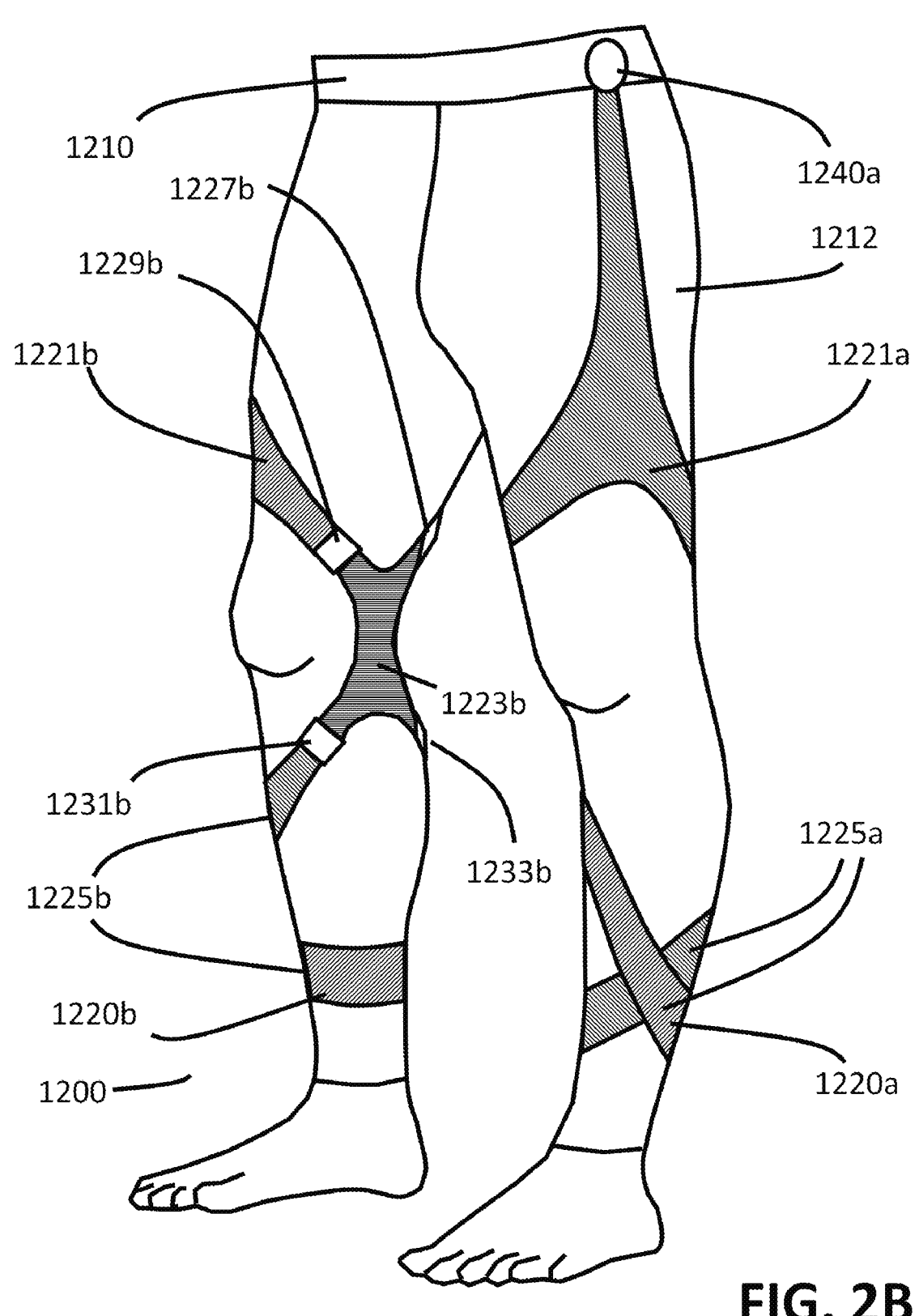

We turn now to a first embodiment of a medial collateral ligament brace garment 1200, which may also be termed a bracing garment, shown in FIG. 2A and FIG. 2B, in which the knee joint of FIG. 1 is addressed by garment 1200 comprising belt 1210, extensible material 1212 forming the basic matrix material of garment 1200, tensioners 1240a and 1240b, and webs of substantially inextensible material 1221a, 1221b, 1225a, and 1225b.

The term "substantially inextensible material" is used herein to describe a material extending in two dimensions that is substantially inextensible in at least a first direction. The material may or may not have a restriction on extensibility in a direction perpendicular to the first direction. Non-limiting examples of such materials include but are not limited to so-called 2-way-stretch fabrics with blends of fabrics including Spandex, Nylon, Dyneema, Kevlar, polyester, Ingeo, olefin fibre, Lyocell, and/or cotton which are woven, knitted, or braided in such a fashion to allow stretch in required dimensions. The "2-way" stretching refers here to stretching in two opposing directions in a first dimension whilst remaining substantially inextensible in any direction perpendicular to the first direction. Other "substantially inextensible materials", including for example without limitation fabrics comprising Dyneema™ fibers in a two-dimensional mesh embedded in a second fabric or in a sandwich structure, may have substantially no extensibility in any direction. The inextensibility is deemed "substantial" in comparison with the inextensibility of the matrix material of the fabric of the garment, the garment fabric being stretchable or extensible in comparison with the "substantially inextensible material". We use herein the term "inextensible web" to describe a web made from a substantially inextensible material.

Broken rectangle 100 indicates the region of the left leg shown in FIG. 1. The webs of inextensible material form part of two independent tension members, being tension member 1220a for the left leg and tension member 1220b for the right leg, each joined to belt 1210. In order to reduce clutter in the drawings, each tension member is labeled only at its lower end in the drawings. Tension member 1220a comprises three webs of inextensible material, being upper inextensible web 1221a disposed on the left thigh, medial inextensible web 1223a disposed on the medial side of the left knee, and lower inextensible web 1225a disposed on the lower left leg, generally defining a curved three-dimensional spatial path which is spatially relating tension member 1220a to at least one ligament of joint 100. Tension member 1220a further comprises tensionable fasteners 1227a and 1229a attaching inextensible web 1221a to inextensible web 1223a. Tension member 1220a further comprises tensionable fasteners 1231a and 1233a attaching inextensible web 1223a to inextensible web 1225a. The same is correspondingly true of tension member 1220b, being comprised of corresponding inextensible webs 1221b, 1223b, and 1225b, as well as four corresponding fasteners, 1227a, 1229a, 1231b and 1233b, all obscured in FIG. 2A but visible in FIG. 2B.

Tension member 1220a may be joined to belt 1210 by means of adjustable tensioner 1240a (obscured in FIG. 2A, but visible in FIG. 2B) which is disposed and configured to allow the tension in tension member 1220b to be adjusted. Tension member 1220b may similarly be joined to belt 1210 by means of adjustable tensioner 1240a which is similarly disposed and configured to allow the tension in tension member 1220b to be adjusted.

Being directed to applying a suitable force to the medial collateral ligament (MCL) 170, tension member 1220a is disposed to apply via inextensible web 1223a a force on the medial side of joint 100, the force on the medial side of the left knee being directed generally toward the lateral side of the left knee. This stabilizes the left knee joint against medial displacement as a result of problems with the medial collateral ligament of the left knee. Correspondingly, tension member 1220b is disposed to apply via inextensible web 1223b a force on the medial side of the right knee joint, the force on the medial side of the right knee being directed generally toward the lateral side of the right knee. This stabilizes the right knee joint against medial displacement as a result of problems with the medial collateral ligament of the right knee. The various tensionable fasteners may be implemented in a variety of well known ways via, for example without limitation, ratchets, cam buckles, laces, straps with buckles, Velcro® fasteners, and the like.

FIG. 2A and FIG. 2B show the left and right knees both being stabilized by respective independent tension members 1220a and 1220b. In some embodiments there may be a tension member on only one of the two legs. Alternatively, there may be two tension members, one for each leg or knee, but only one is put under tension to apply to an affected or unstable knee. It will be understood by practitioners in the field that, if there is only a single tension member and it is applied to, for example, the left leg, then turning the garment inside out will render the tension member correctly arranged for application to the right leg to serve as stabilizing system for the right knee instead of the left knee.

Figure 3A:
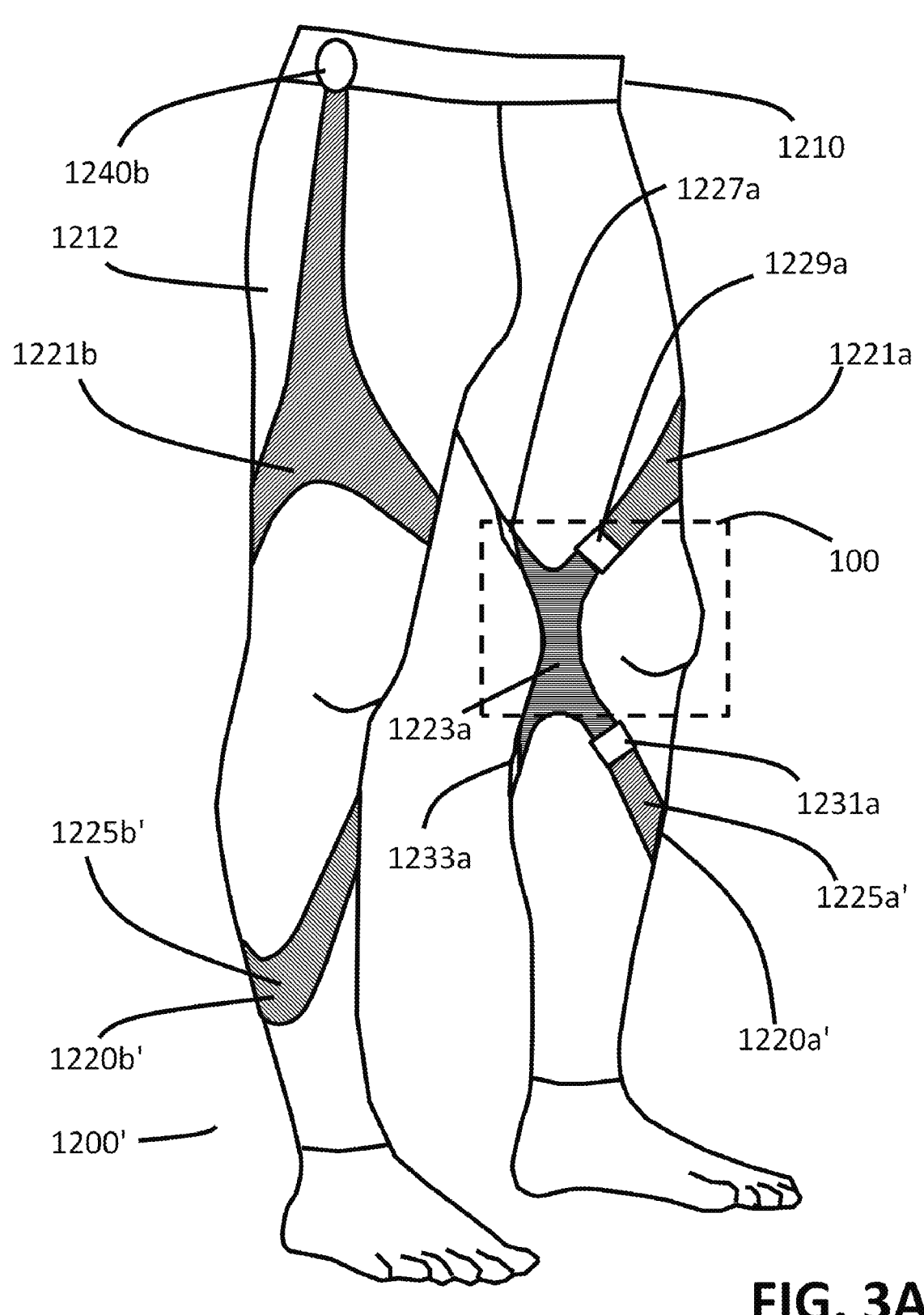
FIG. 3A and FIG. 3B are drawings showing different views of an embodiment of a medial collateral ligament bracing garment for protecting the human knee in which a different lower inextensible web is employed.
Figure 3B:
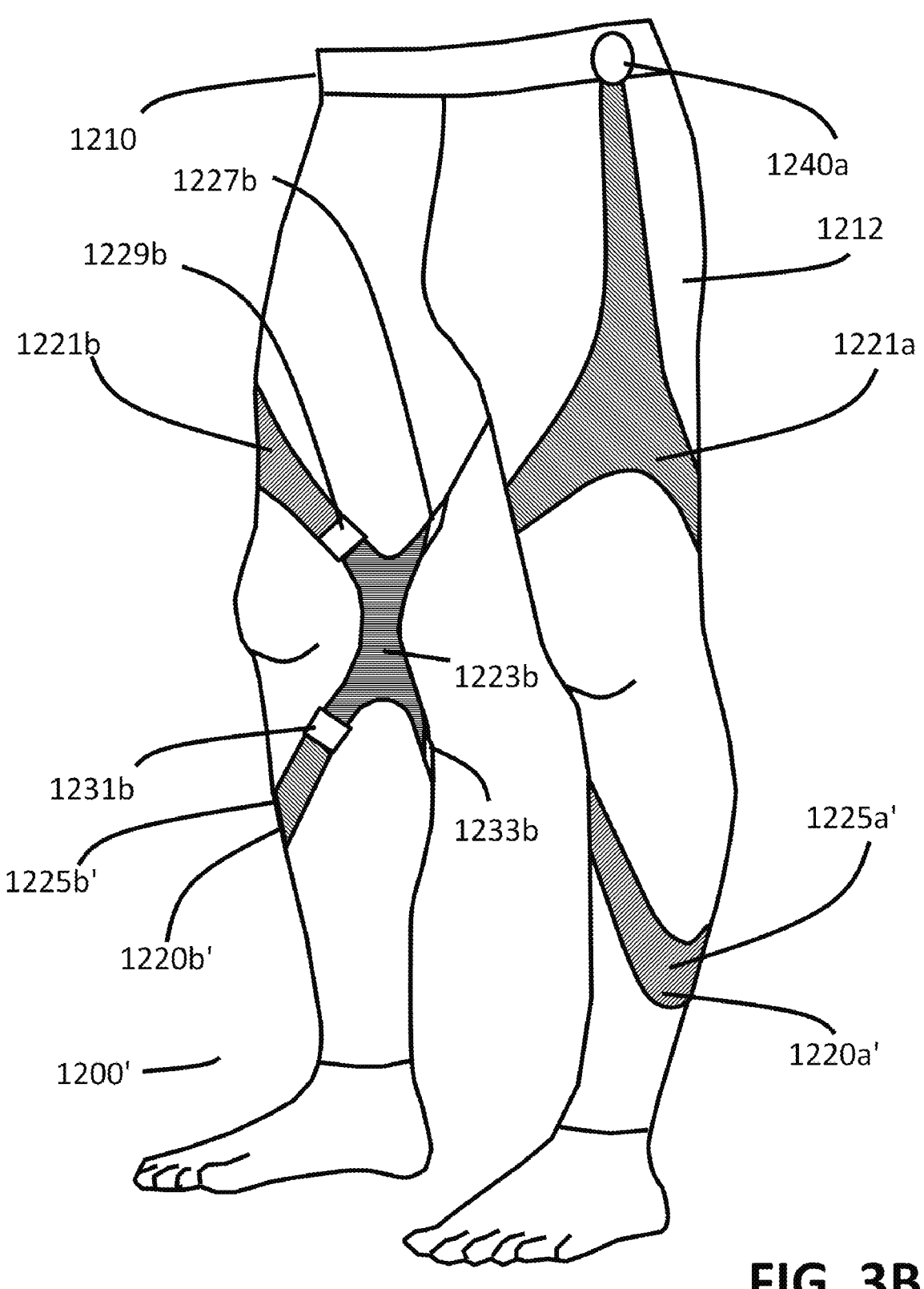

In FIG. 2A and FIG. 2B lower inextensible webs 1225a and 1225b are shown as looping around the leg below the triceps surae. In another embodiment of garment 1200', shown in FIG. 3A and FIG. 3B, lower inextensible webs 1225a' and 1225b' do not loop around the leg, but simply extend partially around the leg below the triceps surae and effectively anchor themselves to the triceps surae. In order to reduce clutter in the drawings, each tension member is labeled only at its lower end in the drawings, being 1220a' for the tension member on left leg and 1220b' for the tension member on the right leg.

Figure 4A:
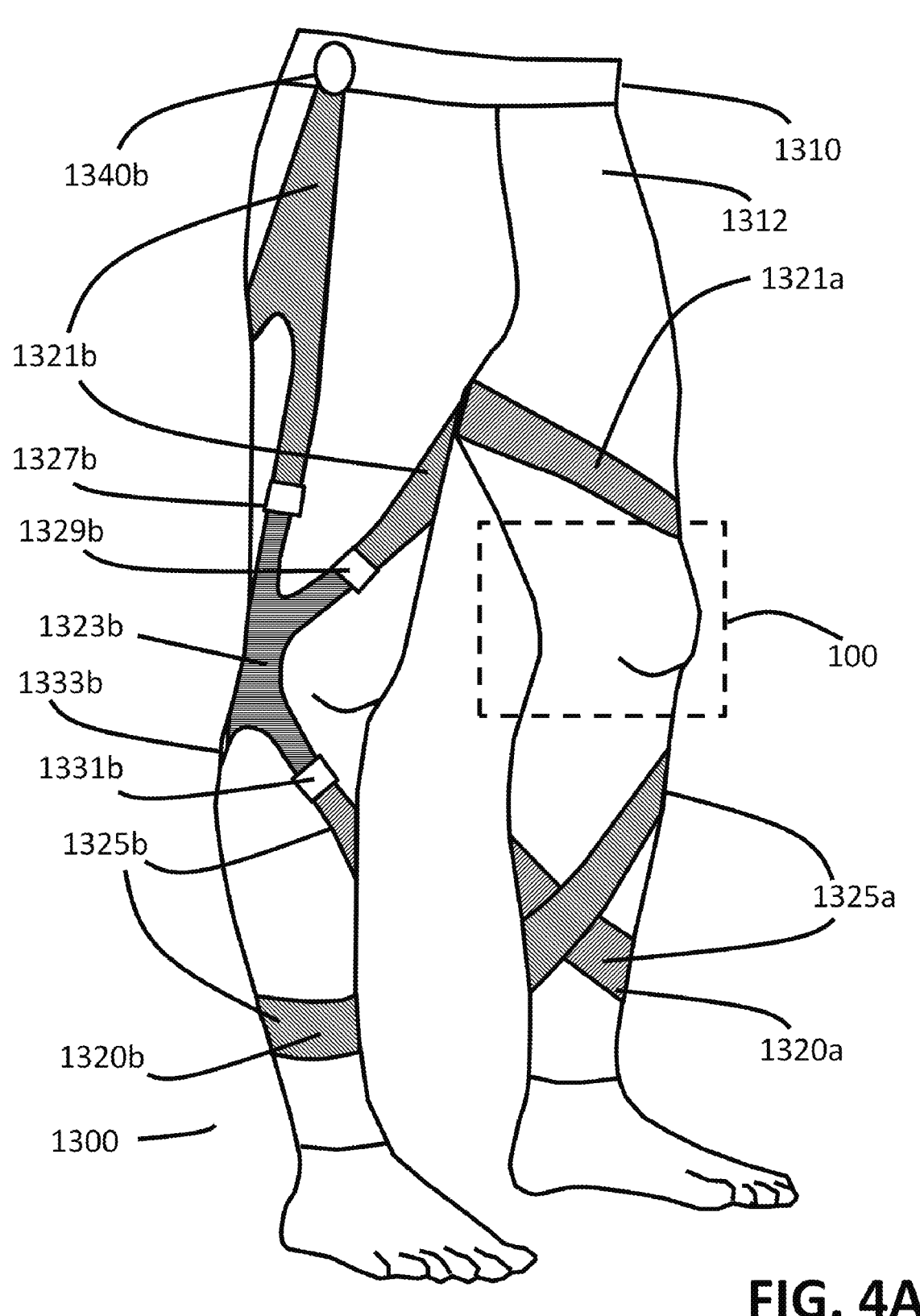
FIG. 4A and FIG. 4B are drawings showing different views of an embodiment of a lateral collateral ligament bracing garment for protecting the human knee.
Figure 4B:
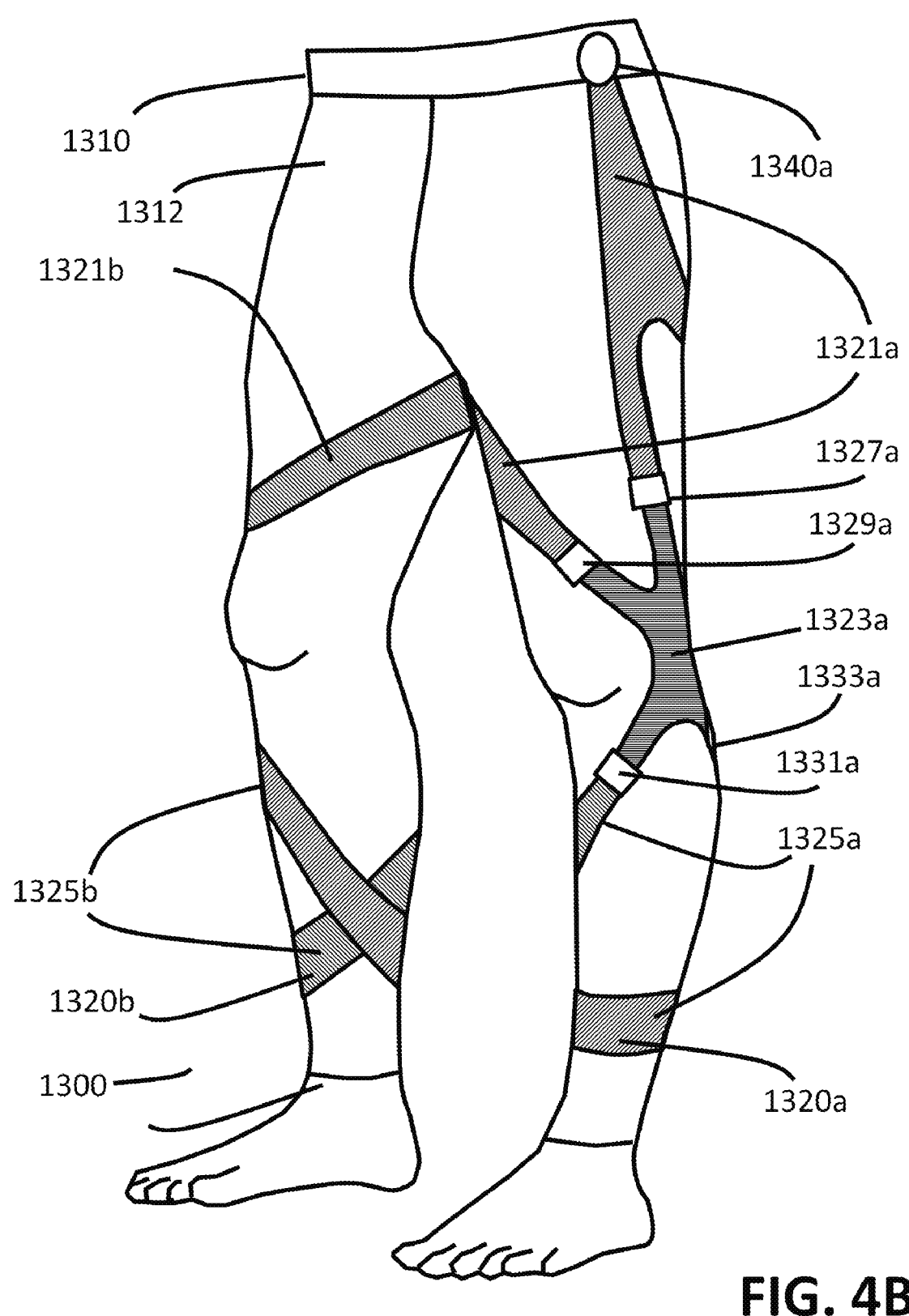

We turn now to a first embodiment of lateral collateral ligament brace garment 1300 shown in FIG. 4A and FIG. 4B, in which the knee joint of FIG. 1 is addressed by garment 1300 comprising belt 1310, extensible fabric 1312 forming the basic matrix material of garment 1300, webs of inextensible material, and tensioner 1340a (visible in FIG. 4B). Broken rectangle 100 indicates the region of the left leg shown in FIG. 1. The webs of inextensible material form part of two independent tension members, being tension member 1320a for the left leg and tension member 1320b for the right leg, each joined to belt 1310. Tension member 1320a comprises three webs of inextensible material, being upper inextensible web 1321a disposed on the left thigh and passing around it, lateral inextensible web 1323a disposed on the lateral side of the left knee, and lower inextensible web 1325a disposed on the lower left leg. Tension member 1320a further comprises tensionable fasteners 1327a and 1329a attaching inextensible web 1321a to inextensible web 1323a. Tension member 1320a further comprises tensionable fasteners 1331a and 1333a attaching inextensible web 1323a to inextensible web 1325a. The same is correspondingly true of tension member 1320b, being comprised of corresponding inextensible webs 1321b, 1323b, and 1325b, as well as four corresponding fasteners, 1327a, 1329a, 1331b and 1333b, all obscured in FIG. 4A but visible in FIG. 4B. In order to reduce clutter in the drawings, each tension member is labeled only at its lower end in the drawings, being 1320a for the tension member on left leg and 1320b for the tension member on the right leg.

Tension member 1320a may be joined to belt 1310 by means of adjustable tensioner 1340a (obscured in FIG. 4A, but visible in FIG. 4B) which is disposed and configured to allow the tension in tension member 1320b to be adjusted. Tension member 1320b may similarly be joined to belt 1310 by means of adjustable tensioner 1340a which is similarly disposed and configured to allow the tension in tension member 1320b to be adjusted.

Being directed to applying a suitable force to the lateral collateral ligament (LCL) 180, tension member 1320a is disposed to apply via inextensible web 1323a a force on the lateral side of joint 100, the force on the lateral side of the left knee being directed generally toward the medial side of the left knee. This stabilizes the left knee joint against lateral displacement as result of problems with the lateral collateral ligament of the left knee. Correspondingly, 1320b is disposed to apply via inextensible web 1323b a force on the lateral side of the right knee joint, the force on the lateral side of the right knee being directed generally toward the medial side of the right knee. This stabilizes the right knee joint against lateral displacement as result of problems with the lateral collateral ligament of the right knee. The various tensionable fasteners may be implemented in a variety of well known ways via, for example without limitation, ratchets, cam buckles, laces, straps with buckles, Velcro® fasteners, and the like.

In FIG. 4A and FIG. 4B lower inextensible webs 1325a and 1325b are shown as looping around the leg below the triceps surae. As explained with reference to the medial collateral ligament brace garment of FIG. 2A and FIG. 2B, the lower inextensible webs may simply extend partially around the leg once below the triceps surae and effectively anchor themselves to the triceps surae, as for the medial collateral ligament brace system of FIG. 3A and FIG. 3B.

In FIG. 4A and FIG. 4B one upper limb of inextensible webs 1323a and 1323b are shown as connected directly to respectively web 1321a and 1321b via respectively fasteners 1327a and 1327b. In this implementation, the particular limbs of webs 1323a and 1323b therefore extend vertically along the thigh. In alternative embodiments, later used in FIG. 8A, FIG. 8B, FIG. 9A and FIG. 9B, web 1321a and 1321b may have extensions that extend around first the anterior, then the medial side, and then the posterior of the corresponding leg to be joined to webs 1323a and 1323b via fasteners 1327a and 1327b respectively. This particular arrangement may be better understood at the hand of FIG. 8A, FIG. 8B, FIG. 9A and FIG. 9B below.

Figure 5A:
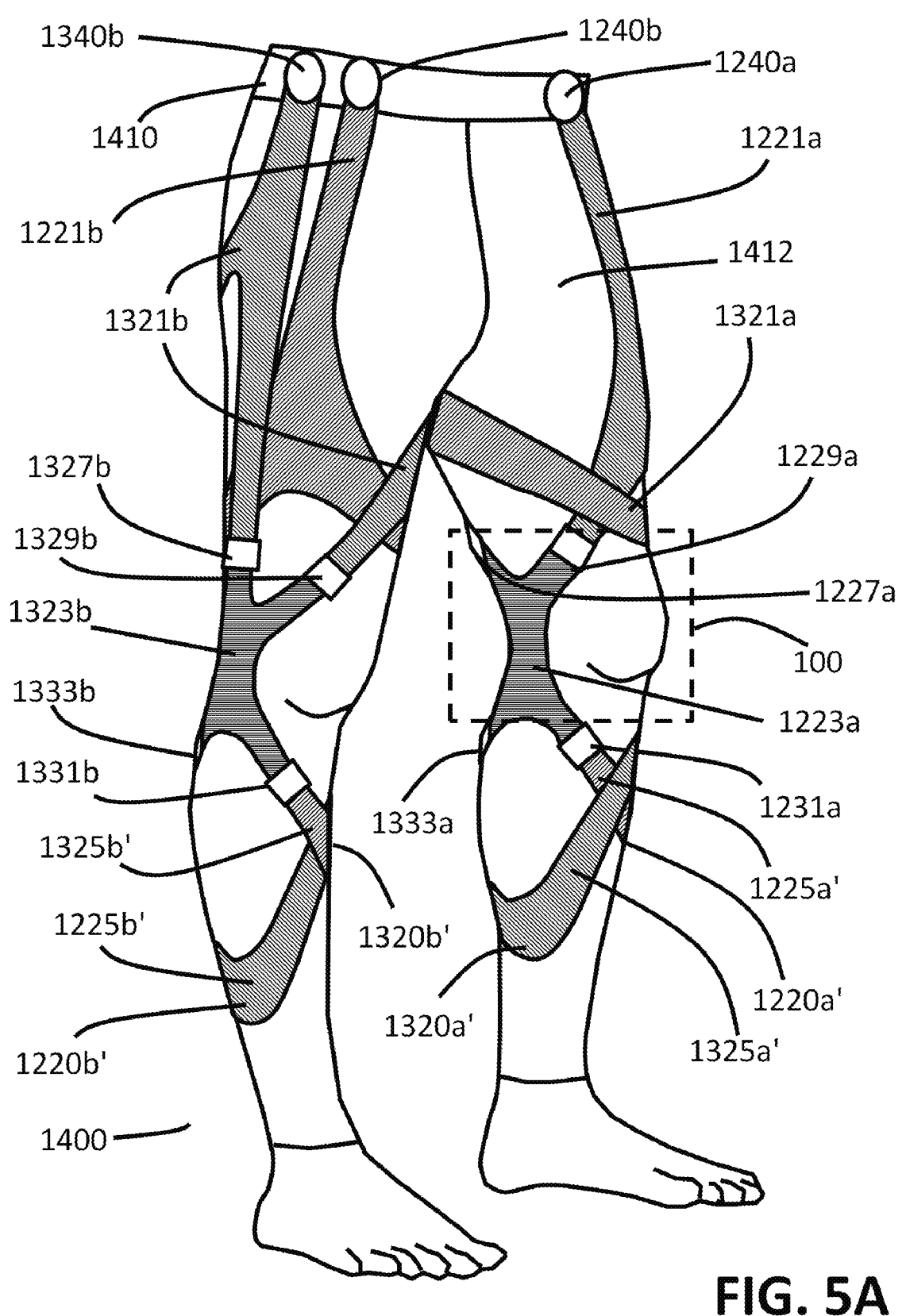
FIG. 5A and FIG. 5B are drawings showing different views of an embodiment of a joint lateral and medial collateral ligament bracing garment for protecting the human knee.
Figure 5B:
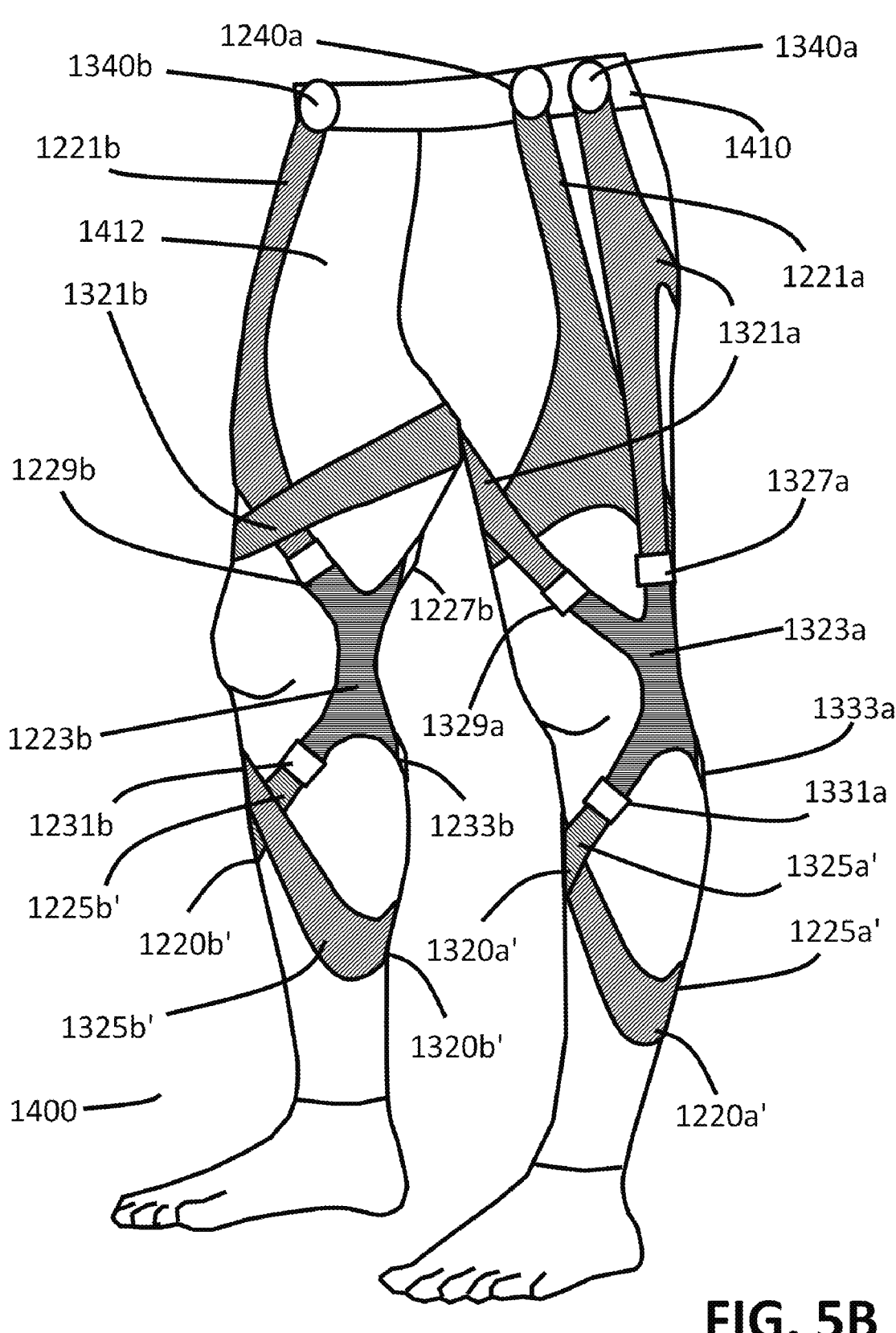

In yet a further embodiment, garment 1400 may have two tension members for a given leg with lateral and medial inextensible webs respectively acting on the lateral and medial sides of a particular knee. FIG. 5A and FIG. 5B show this implementation. The numbering follows the medial collateral ligament brace garment numbering of FIG. 3A and FIG. 3B and the lateral collateral ligament brace garment numbering of FIG. 4A and FIG. 4B, with the following exceptions. The belt is labeled 1410 and the extensible material or fabric of the garment is labeled 1412. The lower inextensible webs of the lateral collateral ligament brace garment numbering are given as 1325a' for the left leg and 1325b' for the right leg, since the lateral collateral ligament brace garment employs the same kind of lower inextensible web as the medial collateral ligament brace garment of FIG. 3A and FIG. 3B. The tensionable members bearing medial collateral ligament braces for the left and right leg are respectively labeled 1320a' and 1320b' proximate their lower ends. As may be seen in FIG. 5A and FIG. 5B, tensioners 1240a and 1240b are moved more toward the anterior of the body to provide space for upper inextensible webs 1221a and 1221b of the lateral collateral ligament brace garment arrangement and for their respective associated tensioners 1340a and 1340b. This embodiment is therefore a direct combination into a single garment of the lateral collateral ligament brace of FIG. 4A and FIG. 4B and the medial collateral ligament brace of FIG. 3A and FIG. 3B, with the exception that the lateral collateral ligament brace has been provided with the same kind of lower inextensible web as the medial collateral ligament brace of FIG. 3A and FIG. 3B.

Based on the garment of FIG. 5A and FIG. 5B, the upper inextensible webs of the two braces may be combined for each leg into one upper inextensible web for each leg. Similarly, the lower inextensible webs of the two braces may be combined for each leg into one lower inextensible web for each leg. The result is garment 1500 of FIG. 6A and FIG. 6B. In this implementation, single lower inextensible web, 1525a for the left leg and 1525b for the right leg, may be connected to both the medial and lateral inextensible webs. Similarly, single upper inextensible web, being 1521a for the left leg and 1521b for the right leg, may be connected to both the medial and lateral inextensible webs. The garment has belt 1510, tensioners 1540a and 1540b. The material forming the basic matrix of the garment is labeled 1512. In this embodiment one leg of the garment has four inextensible webs, being one for the thigh, having four tensionable fasteners for connecting to the medial and lateral inextensible webs, one inextensible web on the medial side of the knee, one inextensible web on the lateral side of the knee, and a single lower inextensible web below the distal portion of the triceps surae. In this embodiment, the lower inextensible web has four tensionable fasteners, two for connecting to the medial inextensible web and two for connecting to the lateral inextensible web. In this embodiment each leg has a single tension member, being 1520a for the left leg and 1520b for the right leg.

Figure 7A:
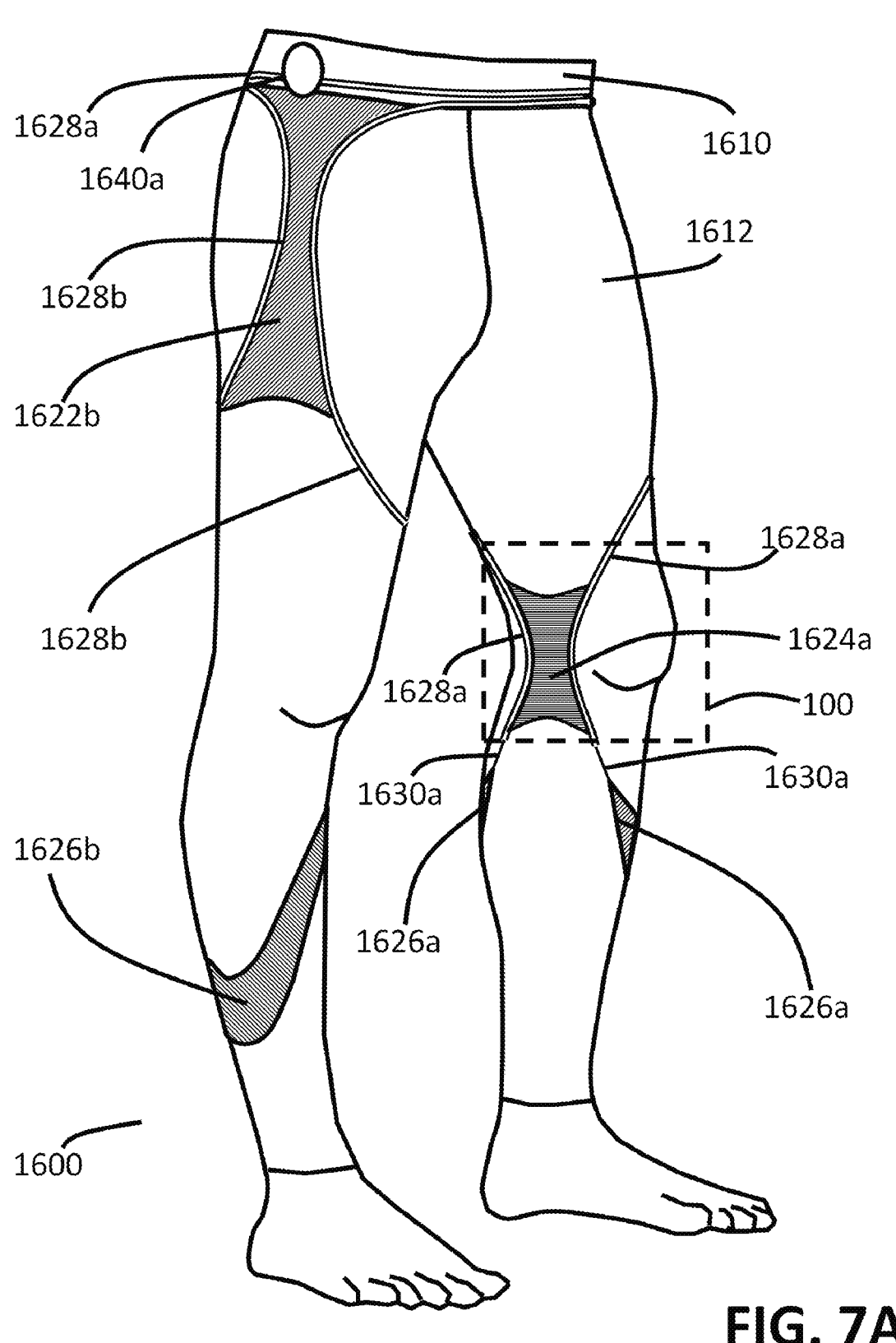
FIG. 7A and FIG. 7B are drawings showing different views of a an embodiment of a medial collateral ligament bracing garment for protecting the human knee in which cables are employed to exert pressure on the medial side of the knee.
Figure 7B:
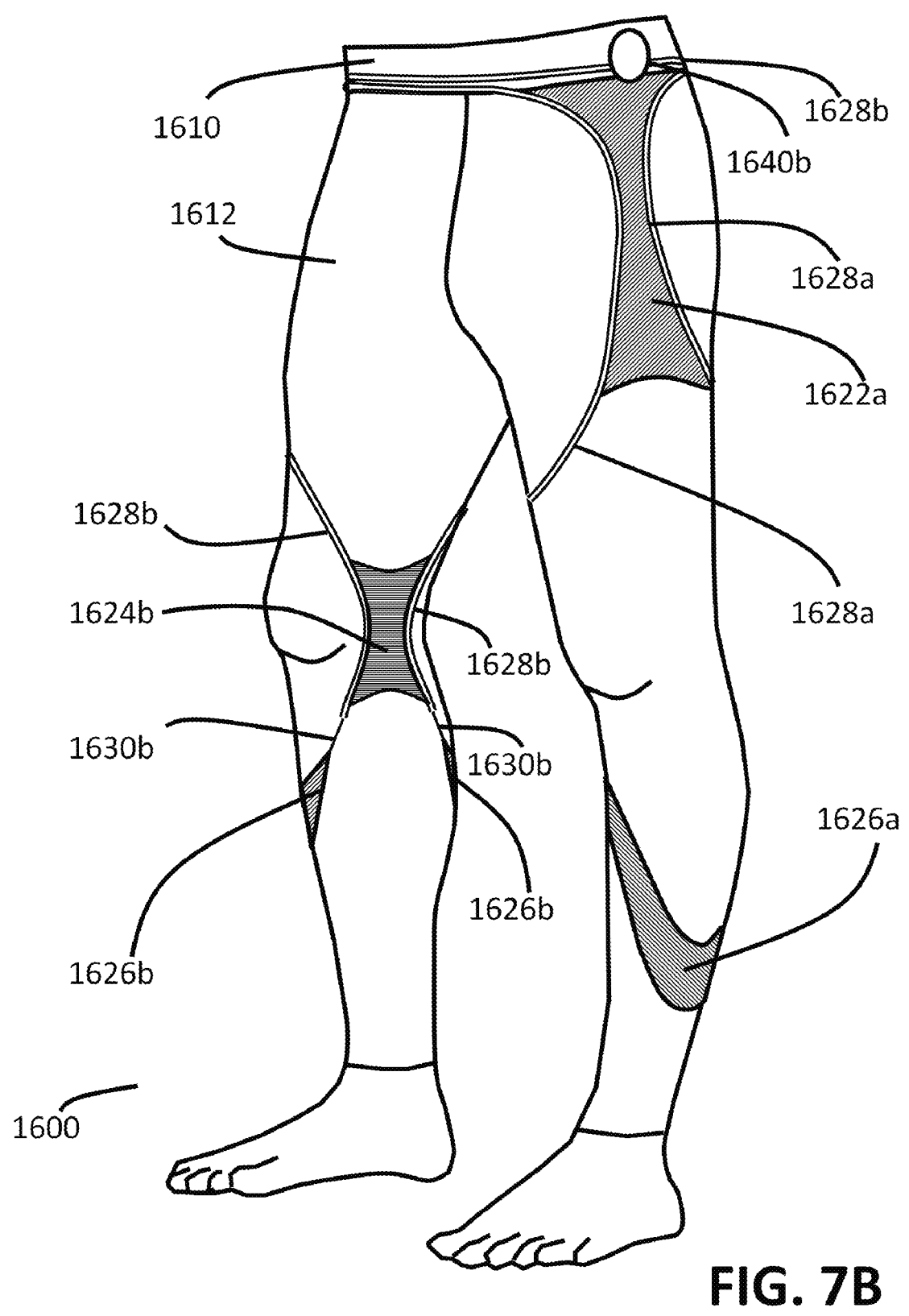

In another embodiment, shown in FIG. 7A and FIG. 7B, the knee joint of FIG. 1 is addressed by medial collateral ligament brace garment 1600 comprising belt 1610, tensioners 1640a for the left leg and 1640b for the right leg, and tension members for the left leg and for the right leg in the form of cables arranged to move in hollow guides within or on inextensible material webs. The cables may be made from a substantially inextensible material, for example without limitation, PTFE, stainless steel, Nylon®, Kevlar®, one or more ultra high molecular weight polyethylene based fiber, and a fiber with a diamond weave. The fiber with a diamond weave may be, for example without limitation, cotton, polyester, polypropylene, and Technora®. Broken rectangle 100 indicates the region of the left leg shown in FIG. 1. In this embodiment, tensioned cables are the means for generating the required force on the knee joint while the webs of inextensible material either serve as anchors to the torso, thigh or lower leg, or they translate to the knee joint the forces generated by the tension in the cables. In order to perform its function, the cable is substantially inextensible.

In FIG. 7A and FIG. 7B, inextensible cable 1630a is attached at its two ends to the two ends of lower inextensible web 1626a. Cable 1630a otherwise runs inside hollow guide 1628a. Inextensible web 1624a, which applies pressure to the medial side of the left leg, is attached at its two horizontal ends to hollow guide 1628a. When the tension in cable 1630a is increased, the pressure on the medial side of the left knee is commensurately increased. In one embodiment, hollow guide 1628a routes cable 1630a around the waist within belt 1610. Upper inextensible material web 1622a assures the positioning of guide 1628a. Tensioner 1640a is disposed within the line of cable 1630a in order to adjust the tension in cable 1630*a*. In the embodiment shown in FIG. 7A and FIG. 7B, tensioner 1640*a* is disposed on the right hip.

Being directed to applying a suitable force to medial collateral ligament (MCL) 170, inextensible web 1624*a* is disposed to apply a force on the medial side of joint 100, the force being directed generally toward the lateral side of the left knee. This stabilizes the left knee joint against medial displacement as result of problems with the medial collateral ligament of the left knee. Correspondingly, inextensible web 1624*b* is disposed to apply a force on the medial side of the right knee, the force being directed generally toward the lateral side of the right knee. This stabilizes the right knee joint against medial displacement as result of problems with the medial collateral ligament of the right knee. To this end, cable 1630*b* is fastened at its two ends to the two ends of lower inextensible material web 1626*b*. Hollow guide 1628*b* routes cable 1630*b* around the waist within belt 1610. Upper inextensible material web 1622*b* assures the positioning of guide 1628*b*. Tensioner 1640*b* is disposed within the line of cable 1630*b* in order to adjust the tension in cable 1630*a*. In the embodiment shown in FIG. 7A and FIG. 7B, tensioner 1640*b* is disposed on the left hip.

Figure 8A:
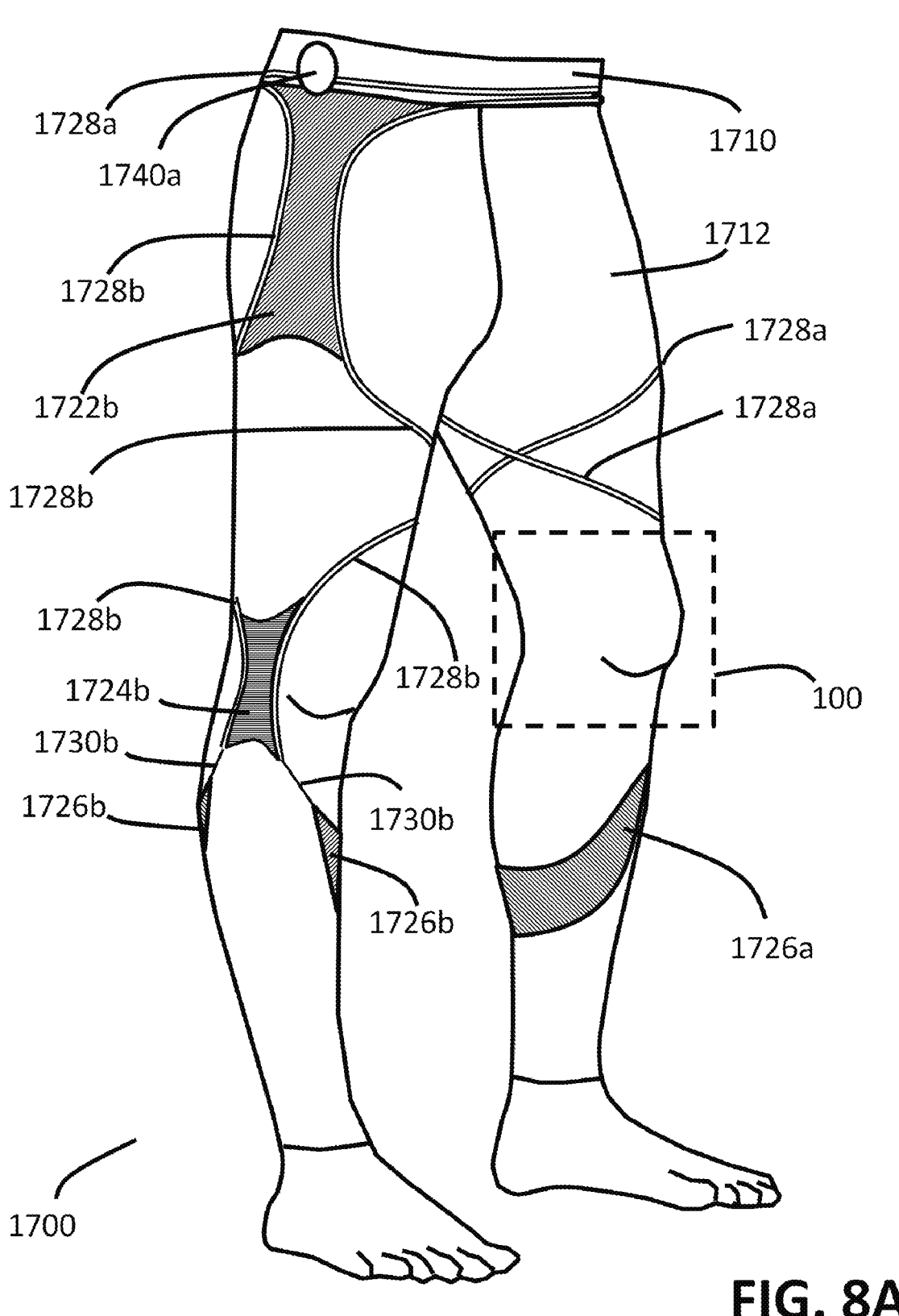
FIG. 8A and FIG. 8B are drawings showing different views of a an embodiment of a lateral collateral ligament bracing garment for protecting the human knee in which cables are employed to exert pressure on the lateral side of the knee.
Figure 8B:
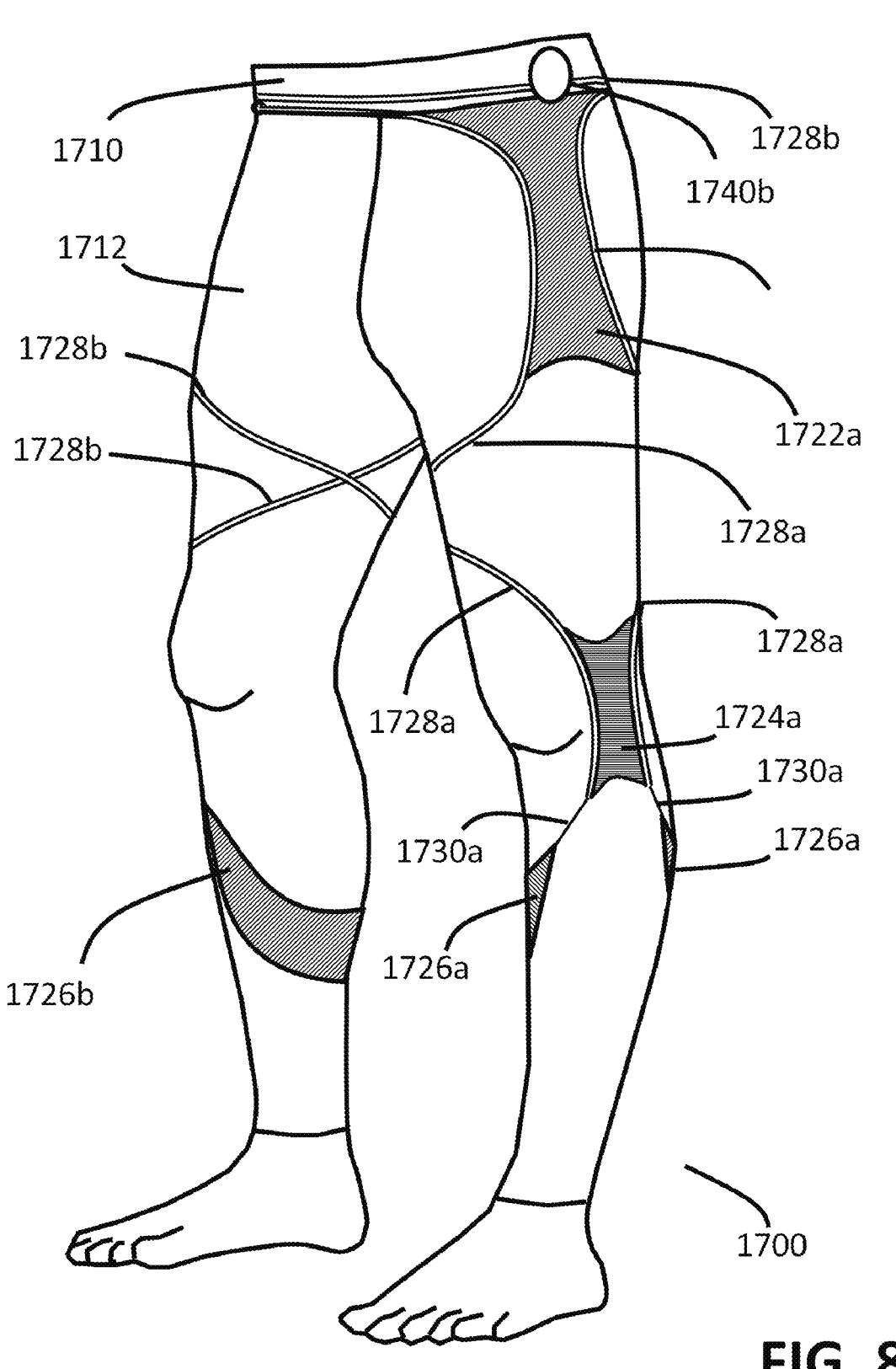

In FIG. 8A and FIG. 8B, the knee joint of FIG. 1 is addressed by lateral collateral ligament brace garment 1700 comprising belt 1710, tensioners 1740*a* for the left leg and 1740*b* for the right leg, and tension members for the left leg and for the right leg in the form of cables arranged to move in hollow guides within or on inextensible material webs. Broken rectangle 100 indicates the region of the left leg shown in FIG. 1. Tensioned cables are the mechanism for generating the required force on the knee joint while the webs of inextensible material either serve as anchors to the torso, thigh or lower leg, or they translate to the knee joint the forces generated by the tension in the cables. In order to perform its function, the cable is substantially inextensible.

In FIG. 8A and FIG. 8B, cable 1730*a* is attached at its two ends to the two ends of lower inextensible web 1726*a*. Cable 1730*a* otherwise runs inside hollow guide 1728*a*. Inextensible web 1724*a*, which applies pressure to the lateral side of the left leg, is attached at its two horizontal ends to hollow guide 1728*a*. When the tension in cable 1730*a* is increased, the pressure on the lateral side of the left knee is commensurately increased. In one embodiment, hollow guide 1728*a* routes cable 1730*a* around the waist within belt 1710. Upper inextensible material web 1722*a* assures the positioning of guide 1728*a*. Tensioner 1740*a* is disposed within the line of cable 1730*a* in order to adjust the tension in cable 1730*a*. In the embodiment shown in FIG. 8A and FIG. 8B, tensioner 1740*a* is disposed on the right hip.

Being directed to applying a suitable force to lateral collateral ligament (LCL) 180, inextensible web 1724*a* is disposed to apply a force on the lateral side of joint 100, the force being directed generally toward the medial side of the left knee. This stabilizes the left knee joint against lateral displacement as result of problems with the lateral collateral ligament of the left knee. Correspondingly, inextensible web 1724*b* is disposed to apply a force on the lateral side of the right knee, the force being directed generally toward the medial side of the right knee. This stabilizes the right knee joint against lateral displacement as result of problems with the lateral collateral ligament of the right knee. To this end, cable 1730*b* is fastened at its two ends to the two ends of lower inextensible material web 1726*b*. Hollow guide 1728*b* routes cable 1730*b* around the waist within belt 1710. Upper inextensible material web 1722*b* assures the positioning of guide 1728*b*. Tensioner 1740*b* is disposed within the line of cable 1730*b* in order to adjust the tension in cable 1670*a*. In the embodiment shown in FIG. 8A and FIG. 8B, tensioner 1740*b* is disposed on the left hip.

Figure 6A:
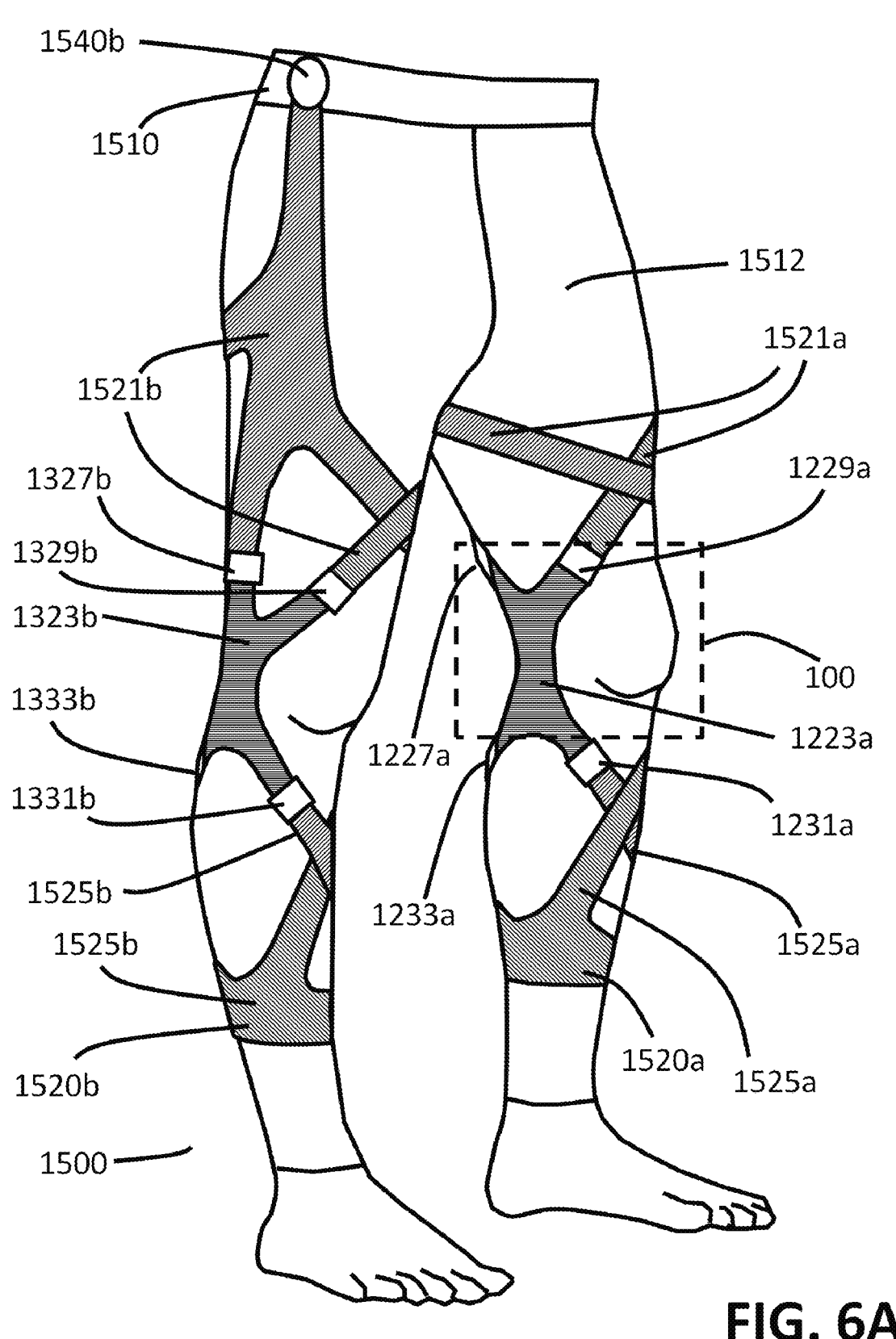
FIG. 6A and FIG. 6B are drawings showing different views of another embodiment of a joint lateral and medial collateral ligament bracing garment for protecting the human knee in which the upper and lower inextensible webs of each leg are combined into single webs.
Figure 6B:
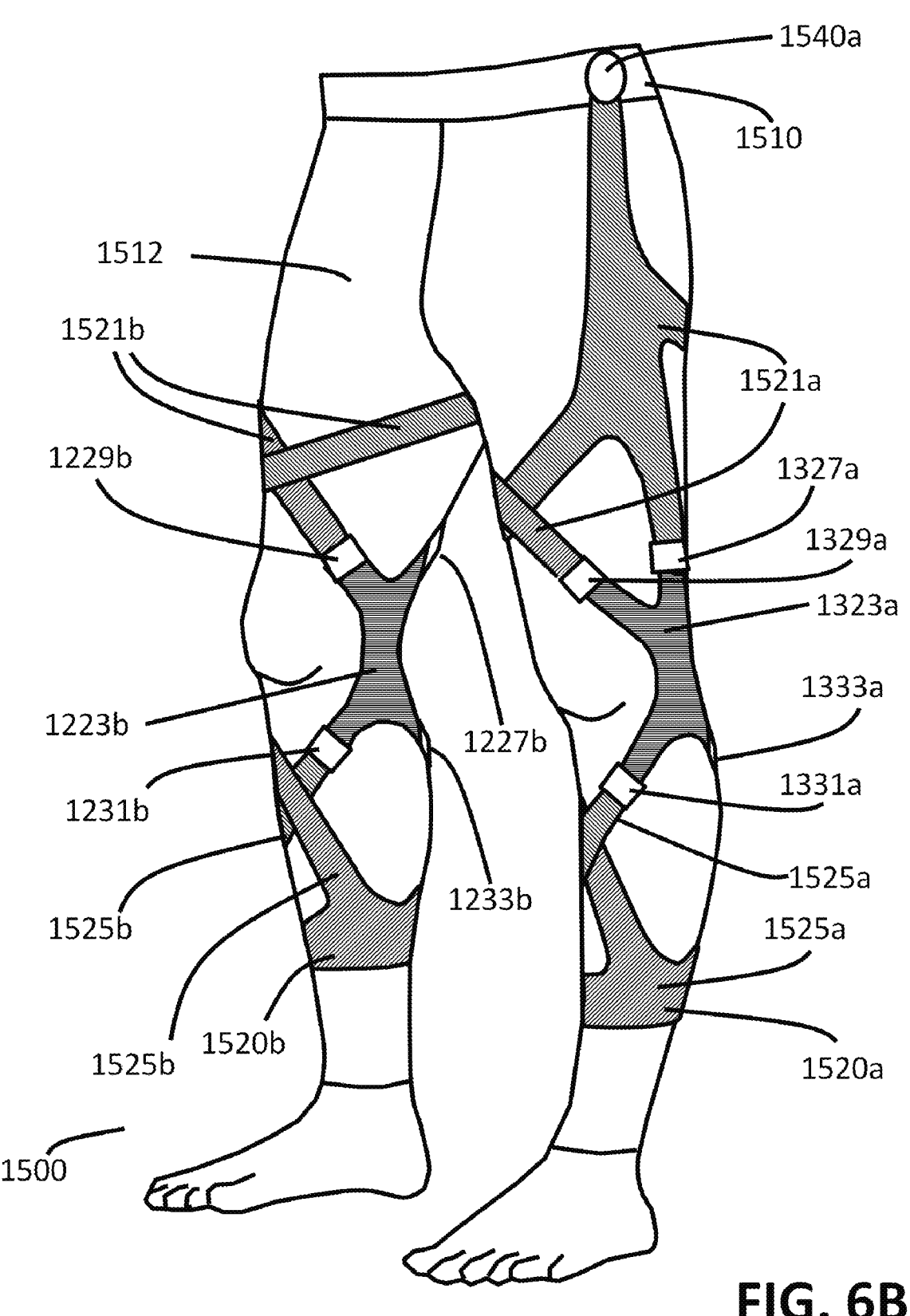
Figure 9A:
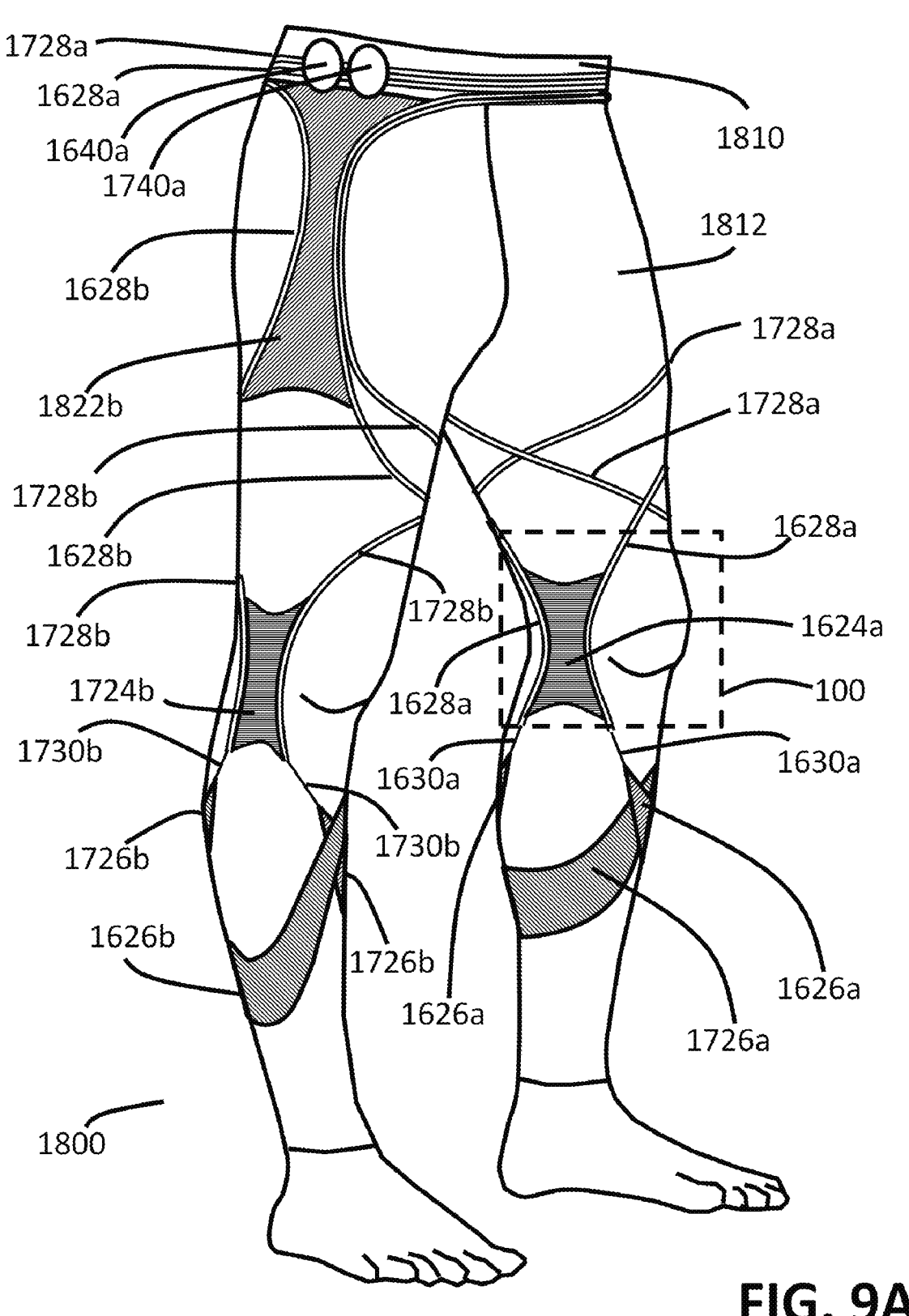
FIG. 9A and FIG. 9B are drawings showing different views of a an embodiment of a combined lateral and medial collateral ligament bracing garment for protecting the human knee in which cables are employed to exert pressure on the lateral and medial sides of the knee.
Figure 9B:
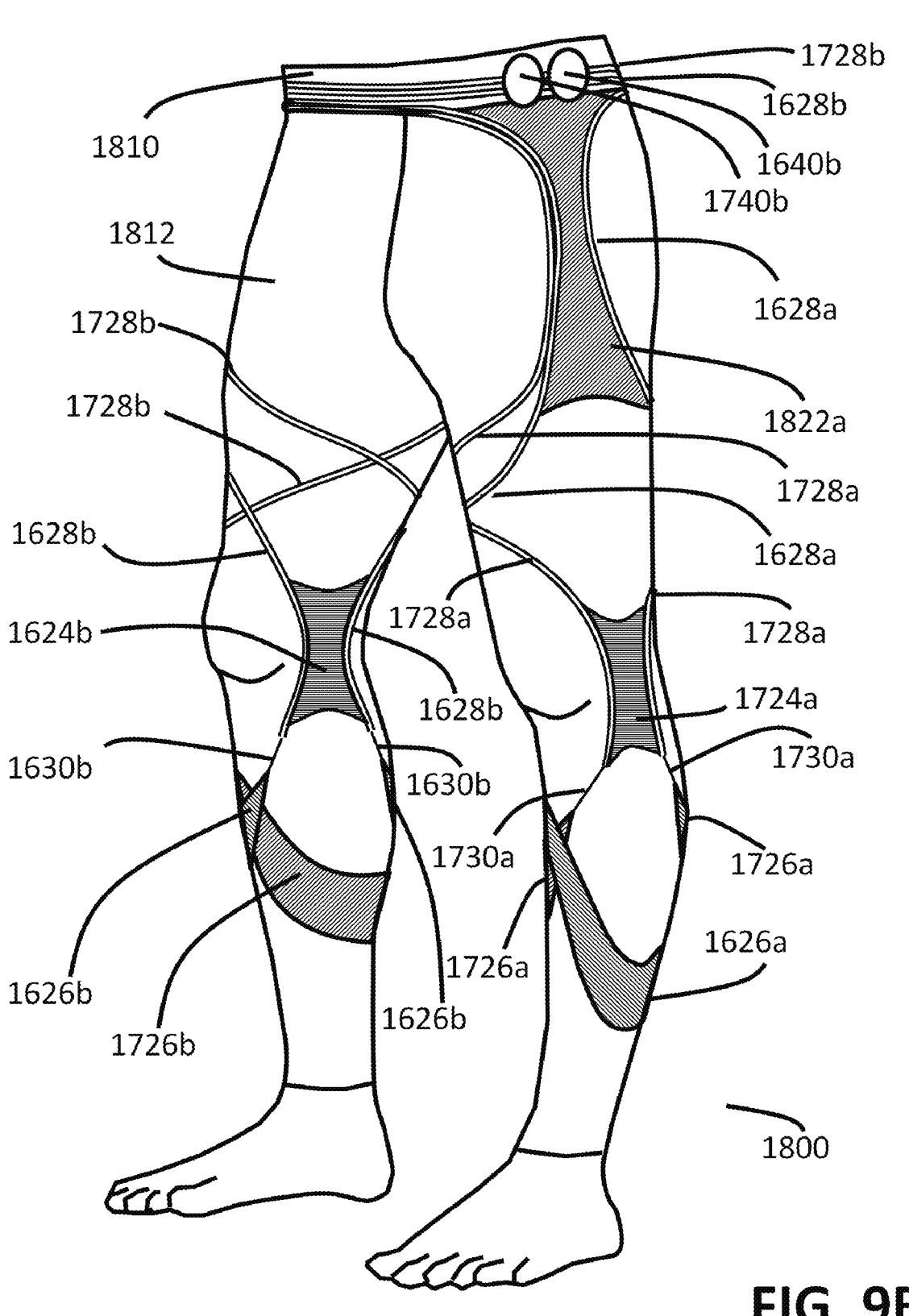

In yet a further embodiment, garment 1800 may have two tension members for a given leg with lateral and medial inextensible webs respectively acting on the lateral and medial sides of a particular knee. FIG. 9A and FIG. 9B show this implementation. The numbering follows the medial collateral ligament brace garment numbering of FIG. 7A and FIG. 7B and the lateral collateral ligament brace garment numbering of FIG. 8A and FIG. 8B, with the following exceptions. The belt is labeled 1810, the extensible material or fabric of the garment is labeled 1812, and the upper inextensible web is labeled 1822*a* and 1822*b* for left and right legs respectively. As may be seen in FIG. 9A and FIG. 9B, the tensioners 1640*a*, 1640*b*, 1740*a* and 1740*b* are relocated slightly from their positions in the earlier drawings in order to accommodate four of these devices. This embodiment is in its effect a direct combination into a single garment of the lateral collateral ligament brace of FIG. 8A and FIG. 8B and the medial collateral ligament brace of FIG. 7A and FIG. 7B, with the exception that the upper inextensible webs of the earlier diagrams have been combined into a single web. The two lower inextensible webs on each leg may be combined in the same arrangement as shown in FIG. 6A and FIG. 6B.

Figure 10A:
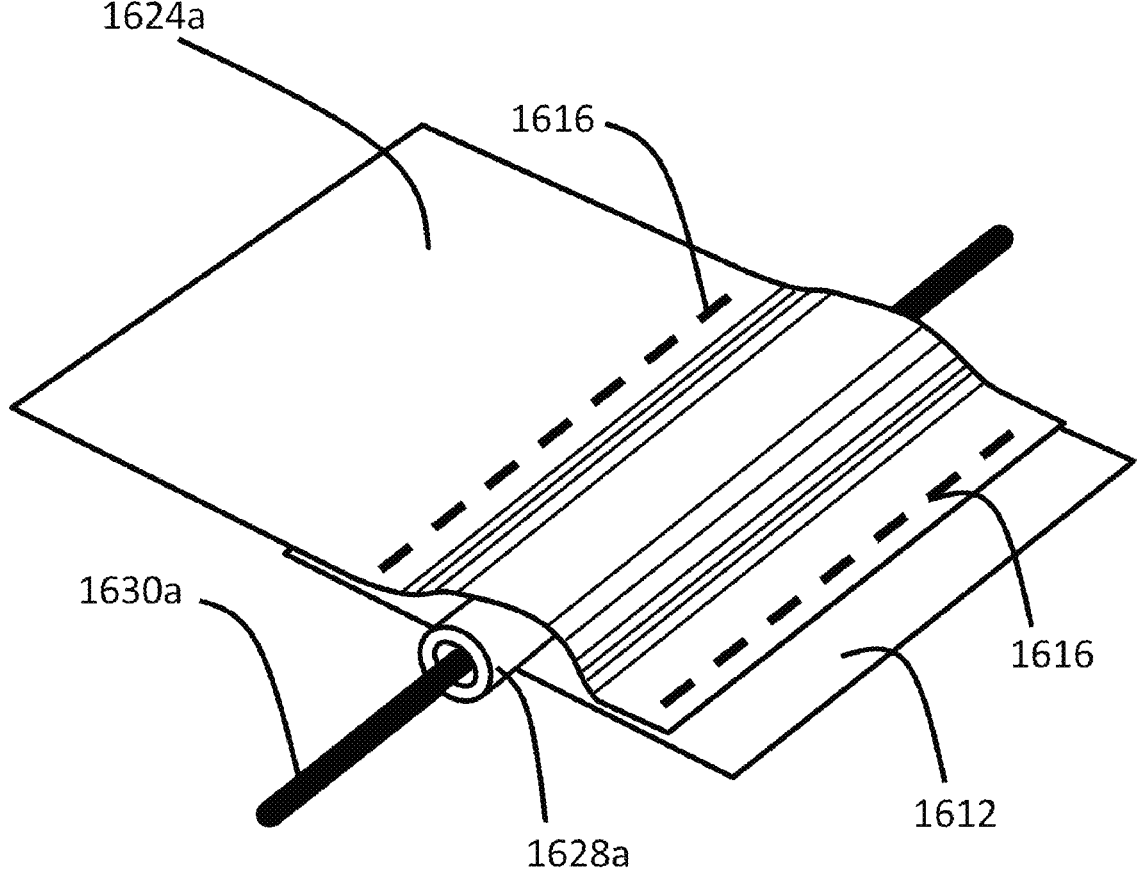
FIG. 10A, FIG. 10B and FIG. 10C are drawings of different embodiments of cable and guide systems for the bracing garments of FIG. 7A, FIG. 7B, FIG. 8A, FIG. 8B, FIG. 9A and FIG. 9B.
Figure 10B:
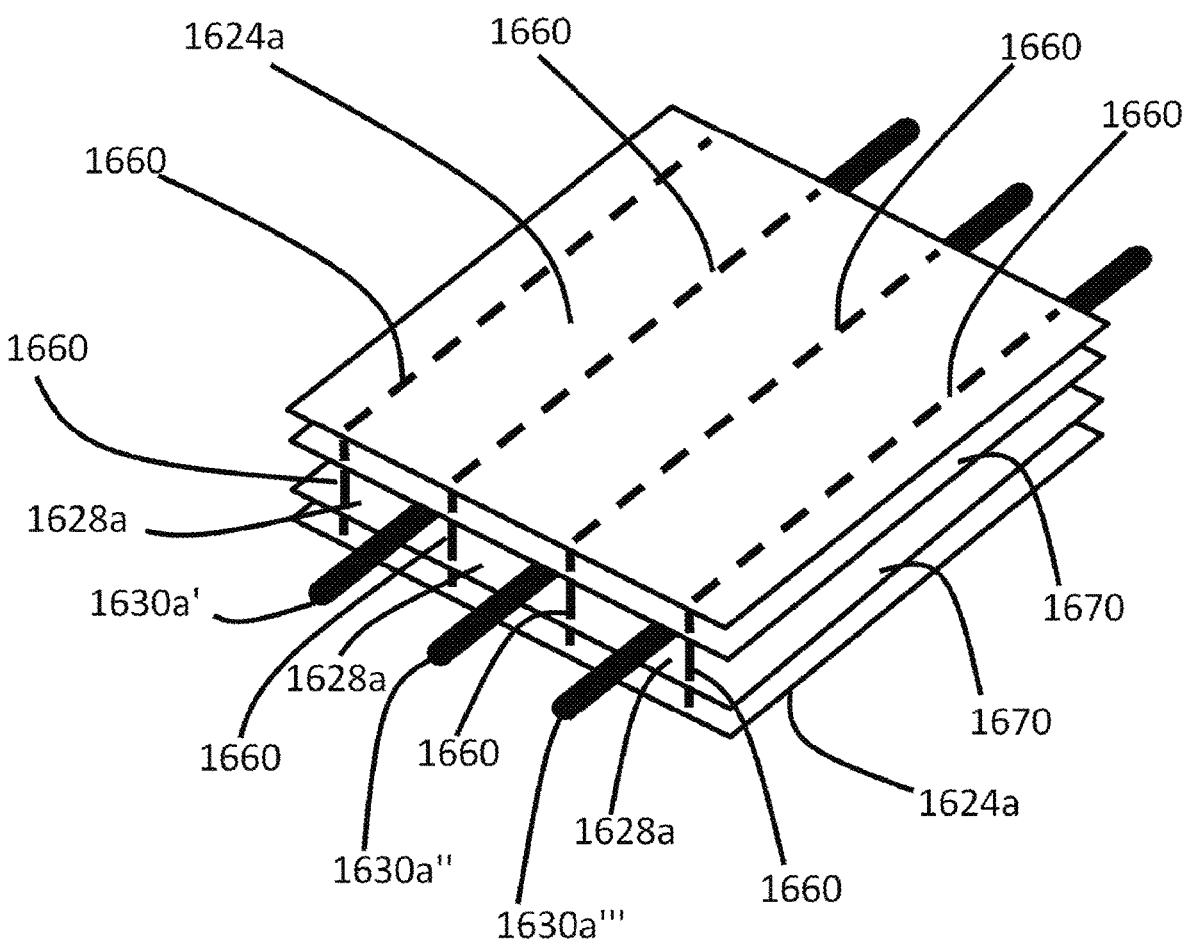
Figure 10C:
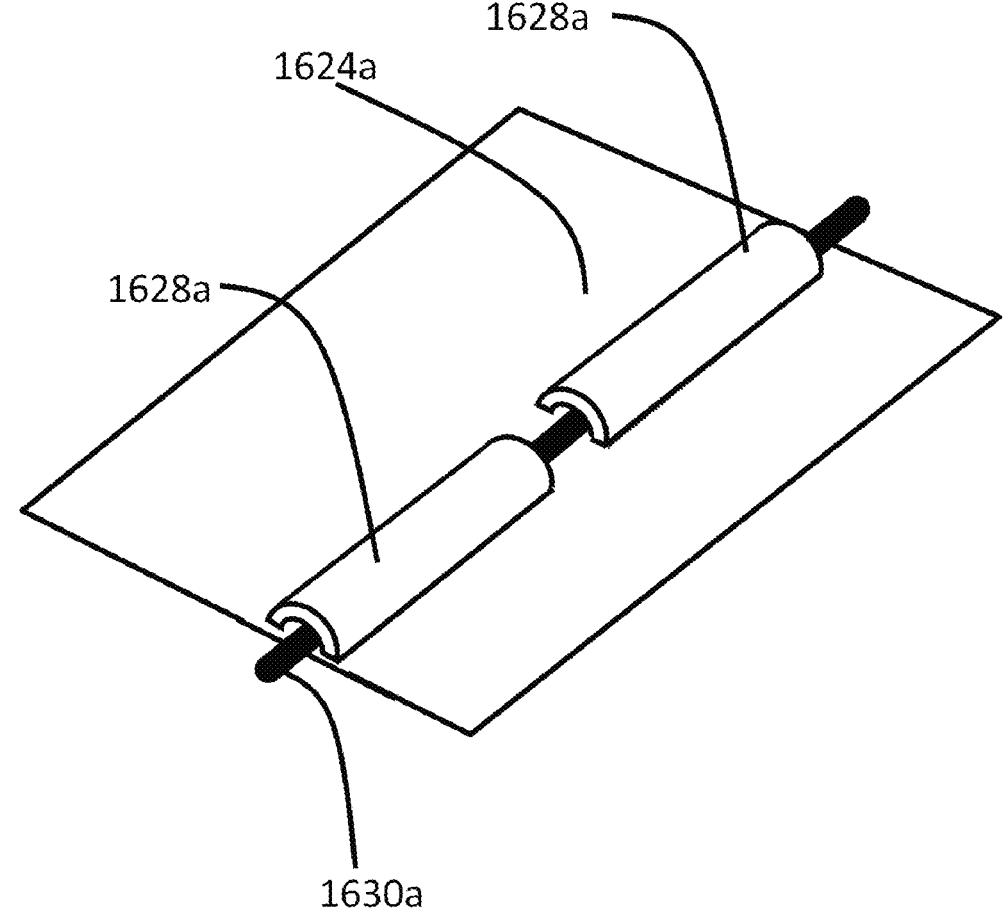

FIG. 10A, FIG. 10B, and FIG. 10C show different implementations of guides 1628*a*, 1628*b*, 1728*a*, and 1728*b* for use respectively with the cables 1630*a*, 1630*b*, 1730*a*, 1730*b* of FIG. 7A, FIG. 7*b*, FIG. 8A, FIG. 8B, FIG. 9A and FIG. 9B. Using the elements of FIG. 7A as example, FIG. 10A shows a seam at the joint created by stitches 1616 between matrix fabric 1612 of garment 1600 and medial collateral web 1624*a*, with guide 1628*a* extending along the seam in the form of tube 1628*a*. Cable 1630*a* extends longitudinally through tube 1628*a*. The material of tube 1628*a* is selected to have a low coefficient of friction with cable 1630*a*. In a more general case, there may be a plurality of joints, each having tube 1628*a* extending longitudinally along it and each tube 1628*a* having a strand of cable 1630*a* extending longitudinally along it. In FIG. 10A, tube 1628*a* is shown as circular in cross-section, but in other embodiments it may have any suitable cross-section that allows the strand of cable 1630*a* to move substantially freely, while simultaneously making tube 1628*a* compatible with the ergonomic requirements to which the garment is subject. One suitable cross-section is semi-circular, or a smaller segment of a circle with enough curvature to accommodate the strand of cable 1630*a*, yet be flat on one side so as to be easily integrated in matrix material 1612 of garment 1600. Tube 1628*a* may be collated, which allows very low friction, but inextensible tubing to be employed. Example materials for tubing 1628*a* include, but are not limited to Teflon® and silica. In a related embodiment, the strand of cable 1630*a* is simply sandwiched between two strips of low fiction material inside a stitched seam or joint. The same arrangements may be applied to the cables and guides of FIG. 7B, FIG. 8A, FIG. 8B, FIG. 9A and FIG. 9B.

FIG. 10B shows another embodiment of a way to incorporate cable 1630*a* of FIG. 7A within the inextensible material of medial collateral web 1624*a* of garment 1600. The drawing is an isometric view of the weave of the fabric of web 1624*a*. It shows four rows 1660 of stitching or weave either side of every one of three strands of cable 1630*a* within the matrix material of medial collateral web 1624*a*, but proximate the edge of web 1624*a*. Three strands of cable 1630*a*, being 1630*a'*, 1630*a''*, and 1630*a'''*, are sandwiched between two longitudinal strips 1670 of low friction material held by stitching 1660. In this drawing, the material of web 1624*a* is shown as being two sheets. This should be considered as presented schematically for the sake of clarity, as the material is in practice woven. The fiber of the stitching may be a low friction material so that cable 1630*a* slides on all sides against low friction material. In this embodiment, guides 1628*a* are formed by low friction material strips 1670 and low friction material stitching 1660. The same arrangements may be applied to the cables and guides of FIG. 7B, FIG. 8A, FIG. 8B, FIG. 9A and FIG. 9B.

FIG. 10C shows an embodiment in which guide 1628*a* is attached to the surface of garment 1600 in the form of collated semi-cylindrical tubes 1628*a* and cable 1630*a* routed through tubes 1628*a*. In some embodiments, the bases of the tubes may be closed or may be lined with a low friction material. The same arrangements may be applied to the cables and guides of FIG. 7B, FIG. 8A, FIG. 8B, FIG. 9A and FIG. 9B.

Figure 11:
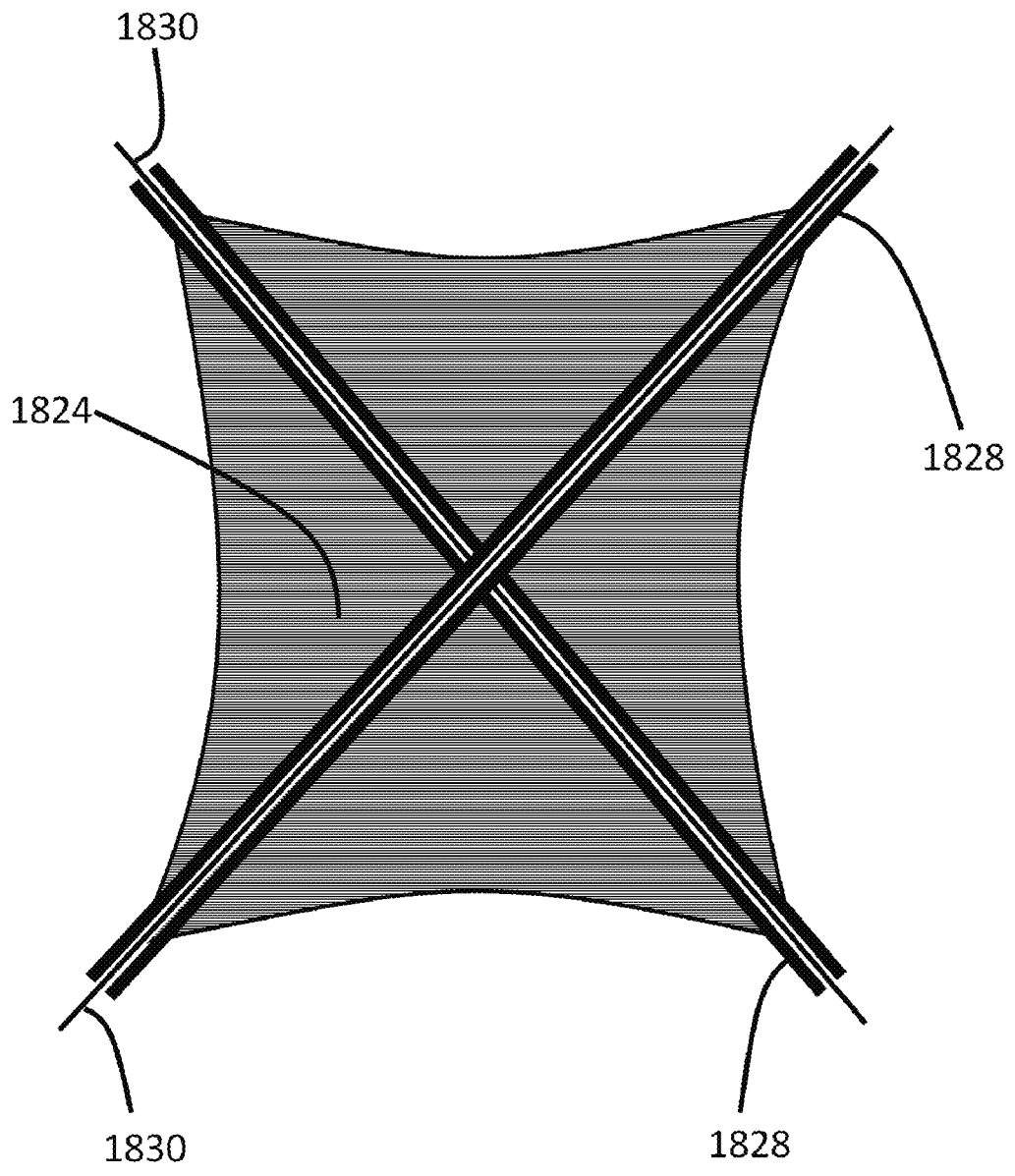
FIG. 11 is a drawing of a web portion of a ligament brace garment arranged to dispose a cable guide to cross over itself on the web.

FIG. 7A, FIG. 7B, FIG. 8A, FIG. 8B, FIG. 9A and FIG. 9B all show guides 1628*a*, 1628*b*, 1728*a*, and 1728*b* as being disposed along the perimeters of webs 1624*a*, 1624*b*, 1724*a*, and 1724*b*. In an alternative embodiment, shown in FIG. 11, guide 1828 may be arranged to cross over itself on medial or lateral collateral web 1824 in order to guide corresponding cable 1830 between diagonally opposing corners of the web. This provides more stabilization of the posterolateral corner and limits excessive internal and external rotation, thereby protecting the anterior cruciate ligament (ACL) 160 of FIG. 1. In FIG. 11 the guide arrangement of FIG. 10A is used. Any other guide arrangement that would cross cable 1830 over itself may be employed.

Figure 12:
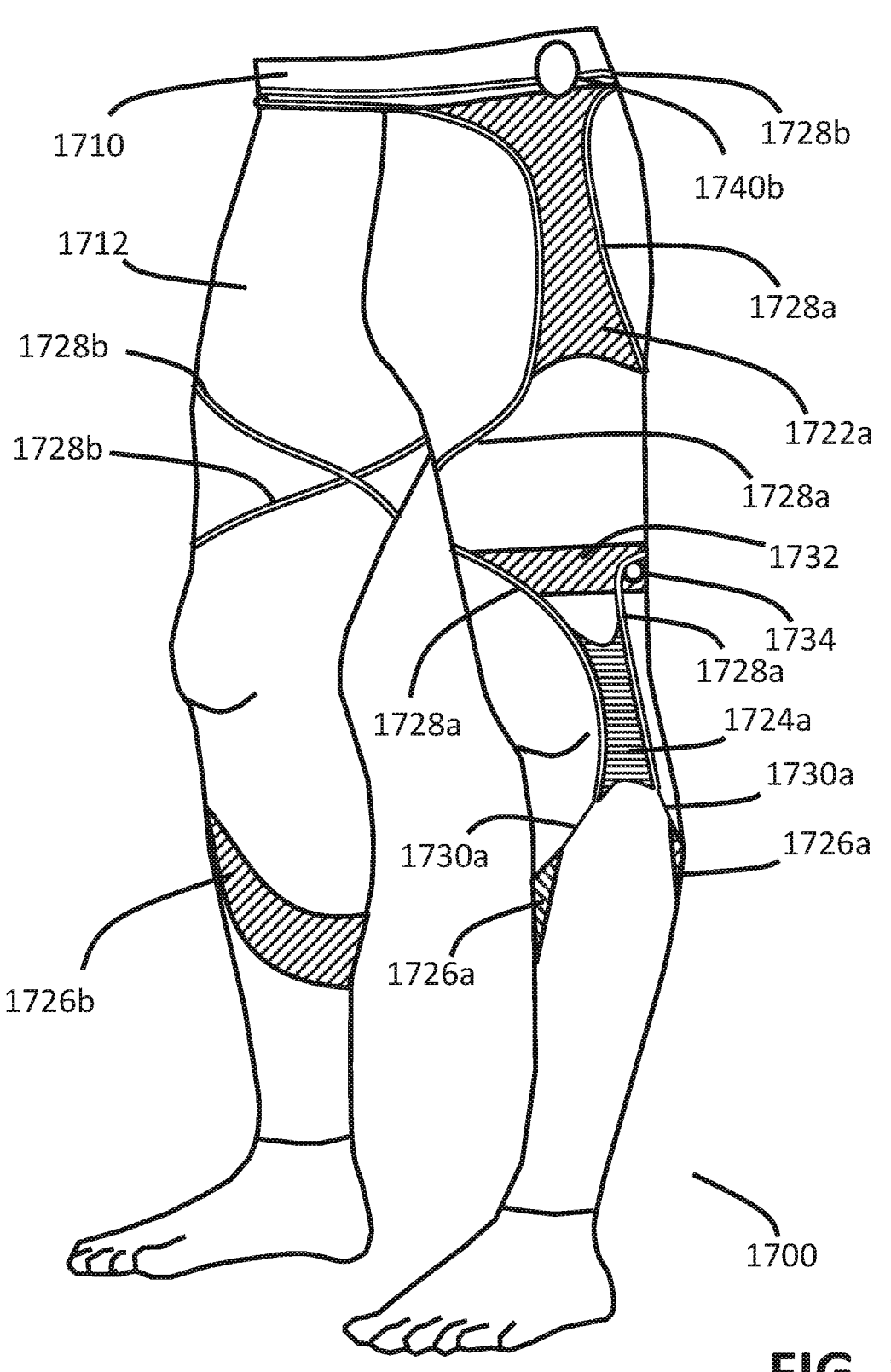
FIG. 12 shows a modification to the embodiment of FIG. 8B.

We turn now to FIG. 12, which shows lateral collateral brace garment of FIG. 8B to which a further inextensible web portion 1732 bearing pulley 1734 has been added, pulley 1734 affixed to inextensible web portion 1732 disposed between the knee and the waist of the user proximate the knee. In order to ensure that suitable tension is maintained in cable 1730*a* when the left leg is bent, guide 1728*a* is routed over pulley 1734, which serves as a tension regulator. Pulley 1734 represents just one implementation of a tension regulator by which tension may be maintained in cable 1730*a* when the leg is bent. Other tension regulators may also be employed, for example without limitation, the guide designs of FIG. 10A, FIG. 10B, and FIG. 10C. Tension regulators may similarly be employed to regulate tension in any of the other tension members disclosed herein.

While the embodiments described herein address the human knee, the devices described herein may with minimal adaptation also be applied to other joints in the human anatomy, for example the elbows, shoulders, and ankles.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed:

1. A brace garment arranged for enveloping at least in part a first knee of a first leg of a human user, the garment comprising a belt configured to be disposed to fit about a waist of the user, a plurality of inextensible web portions, and a first tension member configured to be disposed lon-gitudinally along a corresponding predetermined first curved three-dimensional spatial path within or on a matrix of a garment fabric along the first leg of the user, the first predetermined path spatially relating the first tension member to at least one natural ligament of the first knee, at least one of the plurality of inextensible web portions being disposed by the first tension member to apply pressure to one of a medial and a lateral side of the first knee, wherein the distal end of the first tension member is configured to be disposed to be anchored by the triceps surae of the first leg of the user via a loop of the tension member disposed to extend about the triceps surae of the first leg of the user on one of the medial and lateral side of the first leg of the user and wherein the at least one of the plurality of inextensible web portions is configured to be disposed to apply pressure to the other of the medial and the lateral side of the first knee of the user.

2. The garment of claim 1, further comprising a second tension member disposed longitudinally along a corresponding predetermined second curved three-dimensional spatial path within or on a matrix of a garment fabric along a second leg of the human user, the predetermined second curved three-dimensional spatial path spatially relating the second tension member to at least one natural ligament of a second knee of the second leg, at least one of the plurality of inextensible web portions being disposed by the second tension member to apply pressure to the other of a medial and a lateral side of the second knee.

3. The garment of claim 2, wherein the second tension member has a proximal end and a lateral end, the proximal end of the second tension member anchored to the belt and the distal end of the second tension member configured to be disposed to be anchored by a triceps surae of the first leg of the human user.

4. The garment of claim 3, wherein the distal ends of both the first and the second tension members terminate in a joint inextensible web portion surrounding the first leg below the triceps surae of the first leg.

5. The garment of claim 2, wherein the second tension member is coupled to the belt by an adjustable tensioner.

6. The garment of claim 1, wherein the proximal end of the first tension member is anchored to the belt via a tensioner.

7. The garment of claim 6, wherein the tensioner is an adjustable tensioner disposed and configured to allow the tension in the first tension member to be adjusted.

8. The garment of claim 1, wherein the first tension member comprises an inextensible cable extending along and within one or more hollow guides within or on the matrix of the garment fabric and on or within the matrix of the plurality of inextensible web portions.

9. The garment of claim 8, wherein the inextensible cable crosses over itself on or in the at least one of the plurality of inextensible web portions disposed to apply pressure to one of the medial and the lateral side of the knee.

10. The garment of claim 1, further comprising a tension regulator for maintaining a tension in the first tension member when the first knee of the first leg of the human user is bent.

11. The garment of claim 10, wherein the tension regulator comprises a pulley affixed to an inextensible web portion configured to be disposed between the first knee and the waist of the user proximate the first knee.

12. The garment of claim 1, wherein the first tension member comprises a plurality of the inextensible web portions and tensionable fasteners.

13. The garment of claim 1, further arranged for enveloping at least in part of a second knee of corresponding second leg of the user, the garment comprising a third tension member configured to be disposed longitudinally along a corresponding predetermined third curved three-dimensional spatial path within or on a matrix of a garment fabric along the second leg of the user, the predetermined third path spatially relating the third tension member to at least one natural ligament of the second knee, at least one of the plurality of inextensible web portions being disposed by the third tension member to be configured to apply pressure to one of the medial and a lateral side of a second knee.

14. The garment of claim 1, further comprising a second garment having a second plurality of inextensible web portions, and a second tension member configured to be disposed longitudinally along a corresponding predetermined second curved three-dimensional spatial path within or on a matrix of a garment fabric, the predetermined second path spatially relating the second tension member to at least one natural ligament of the first knee, at least one of the second plurality of inextensible web portions being disposed by the second tension member to apply pressure to the other of the medial and the lateral side of the first knee.

15. The garment of claim 1, wherein the first tension member is coupled to the belt.

16. The garment of claim 1, wherein the first tension member is coupled to the belt by an adjustable tensioner.

17. A brace garment arranged for enveloping at least in part a first knee of a first leg of a human user, the garment comprising a belt configured to be disposed to fit about a waist of the user, a plurality of inextensible web portions, and a first tension member adapted to be disposed longitudinally along a corresponding predetermined first curved three-dimensional spatial path within or on a matrix of a garment fabric along the first leg, the first predetermined path spatially relating the first tension member to at least one natural ligament of the first knee, at least one of the plurality of inextensible web portions being disposed by the first tension member to apply pressure to one of a medial and a lateral side of the first knee, a tension regulator for maintaining a tension in the first tension member when the first knee of the first leg of the human user is bent, wherein the tension regulator comprises a pulley affixed to an inextensible web portion configured to be disposed between the first knee and the waist of the user proximate the first knee.

18. The garment of claim 17, wherein the first tension member has a proximal end and a distal end, the proximal end of the first tension member anchored to the belt and the distal end of the first tension member disposed to be anchored by a triceps surae of the first leg of the user.

19. A brace garment arranged for enveloping at least in part a first joint of a first appendage of a human user, the garment comprising a belt configured to be disposed to fit about a body part of the user, a plurality of inextensible web portions, and a first tension member configured to be disposed longitudinally along a corresponding predetermined first curved three-dimensional spatial path within or on a matrix of a garment fabric along the first appendage, the first predetermined first curved three-dimensional spatial path spatially relating the first tension member to at least one natural ligament of the first joint, at least one of the plurality of inextensible web portions being disposed by the first tension member to apply pressure to one of a first and a second side of the first joint, a tension regulator for maintaining a tension in the first tension member when the first joint of the first appendage of the human user is bent, wherein the tension regulator comprises a pulley affixed to an inextensible web portion configured to be disposed between the first joint and a waist of the user proximate the first joint.

20. A brace garment arranged for enveloping at least in part a first knee of a first leg of a human user, the garment comprising a belt configured to be disposed to fit about a waist of the user, a plurality of inextensible web portions, and a first tension member configured to be disposed longitudinally along a corresponding predetermined first curved three-dimensional spatial path within or on a matrix of a garment fabric along the first leg of the human user, the predetermined first curved three-dimensional spatial path spatially relating the first tension member to at least one natural ligament of the first knee, at least one of the plurality of inextensible web portions being disposed by the first tension member to apply pressure to one of a medial and a lateral side of the first knee, wherein the distal end of the first tension member is configured to be disposed to be anchored by the triceps surae of the user via a loop of the tension member extending more than once around the first leg of the user, the loop configured to be disposed to encircle the first leg of the user below the triceps surae of the first leg of the user.

* * * * *